(12) United States Patent
Wolf et al.

(10) Patent No.: US 7,763,734 B2
(45) Date of Patent: Jul. 27, 2010

(54) SYNTHESIS, STRUCTURE AND USE OF BISOXAZOLIDINES FOR ASYMMETRIC CATALYSIS AND SYNTHESIS

(75) Inventors: Christian Wolf, Arlington, VA (US); Shuanglong Liu, Arlington, VA (US)

(73) Assignee: Georgetown University, Washington, DC (US)

(*) Notice: Subject to any disclaimer, the term of this patent is extended or adjusted under 35 U.S.C. 154(b) by 658 days.

(21) Appl. No.: 11/737,371

(22) Filed: Apr. 19, 2007

(65) Prior Publication Data

US 2007/0265255 A1 Nov. 15, 2007

Related U.S. Application Data

(60) Provisional application No. 60/793,134, filed on Apr. 19, 2006.

(51) Int. Cl.
*C07D 263/52* (2006.01)
*C07D 498/20* (2006.01)
(52) U.S. Cl. ..................................................... 548/216
(58) Field of Classification Search .................. 548/216
See application file for complete search history.

(56) References Cited

OTHER PUBLICATIONS

Nowicka-Scheibe et a., Tetrahedron Letters 48 (2007), 5439-5442.*
Kanatomi et al., Bulletin of the Chemical Society of Japan, vol. 43, No. 1, 226-231 (1970).*
Liu, Shuanglong, et al., "Chiral Amplification Based on Enantioselective Dual-Phase Distribution of a Scalemic bisoxazolidine Catalyst," *Organic Letters* 2007, 9(16), 2965-2968 (ASAP version).
Wolf, Christian, et al., "Bisoxazolidine-Catalyzed Enantioselective Alkynylation of Aldehydes," *J. Am. Chem. Soc.* 2006, 128, 10996-10997.

* cited by examiner

*Primary Examiner*—Rebecca L Anderson
(74) *Attorney, Agent, or Firm*—Dana M. Gordon; Foley Hoag LLP

(57) ABSTRACT

One aspect of the invention relates to chiral bisoxazolidines and their use in asymmetric catalysis. The chiral bisoxazolidines are a novel class of compounds that is expected to find multiple applications, for example, in asymmetric synthesis. For example, a bisoxazolidine ligand enabled the catalytic enantioselective alkynylation and alkylation of a range of aromatic and aliphatic aldehydes, generating chiral propargylic alcohols and secondary alcohols in high yields and enantiomeric excess.

10 Claims, 6 Drawing Sheets

Figure 1
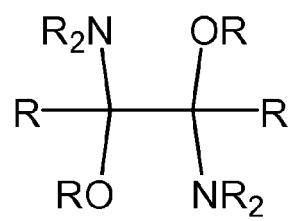
[A]
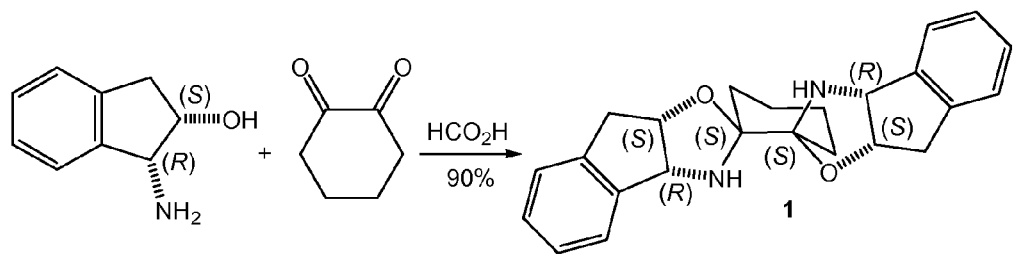
[B]
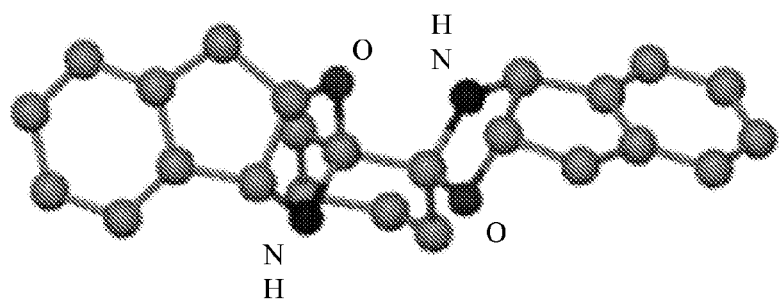
[C]

Figure 2

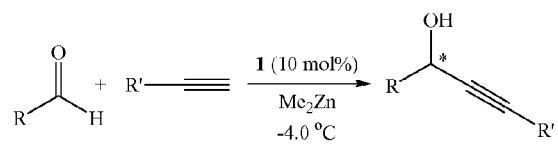

| entry | aldehyde | acetylene | propargylic alcohol | yield[a] (%) | ee[b] (%) |
|---|---|---|---|---|---|
| 1 | PhCHO | Ph-≡ | Ph-C(OH)-≡-Ph | 90 (88)[d] | 93 (91)[d] |
| 2 | 1-naphthyl-CHO | Ph-≡ | 1-Naph-C(OH)-≡-Ph | 91 | 94 |
| 3 | 2-naphthyl-CHO | Ph-≡ | 2-Naph-C(OH)-≡-Ph | 88 | 91 |
| 4 | 4-Cl-C6H4-CHO | Ph-≡ | 4-Cl-C6H4-C(OH)-≡-Ph | 86 | 94 |
| 5 | 4-F-C6H4-CHO | Ph-≡ | 4-F-C6H4-C(OH)-≡-Ph | 92 | 94 |
| 6 | 4-MeO-C6H4-CHO | Ph-≡ | 4-MeO-C6H4-C(OH)-≡-Ph | 95 | 93 |
| 7 | 3-MeO-C6H4-CHO | Ph-≡ | 3-MeO-C6H4-C(OH)-≡-Ph | 88 | 94 |
| 8 | 3-thienyl-CHO | Ph-≡ | 3-thienyl-C(OH)-≡-Ph | 90 | 89 |
| 9 | 2-furyl-CHO | Ph-≡ | 2-furyl-C(OH)-≡-Ph | 94 | 78 |
| 10 | PhCHO | Cy-≡ | Ph-C(OH)-≡-Cy | 87 | 92 |
| 11 | PhCHO | n-Pr-≡ | Ph-C(OH)-≡-n-Pr | 96 | 92 |
| 12 | PhCHO | Cy-≡ | Ph-C(OH)-≡-Cy | 91 | 90 |
| 13 | PhCHO | t-Bu-≡ | Ph-C(OH)-≡-t-Bu | 71 | 95 |
| 14 | PhCHO | cPr-≡ | Ph-C(OH)-≡-cPr | 81 | 89 |
| 15 | Cy-CHO | Ph-≡ | Cy-C(OH)-≡-Ph | 95 | 77 |
| 16 | t-Bu-CHO | Ph-≡ | t-Bu-C(OH)-≡-Ph | 99[c] | 83 |

Figure 3
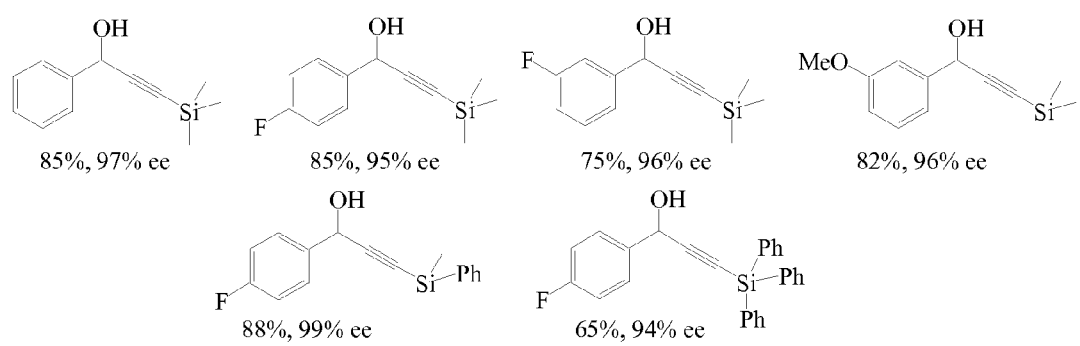
[A]
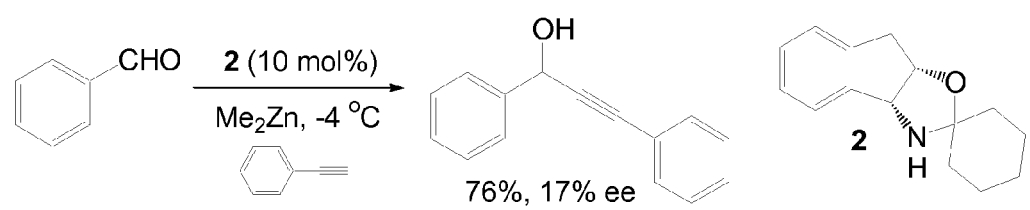
[B]

Figure 4

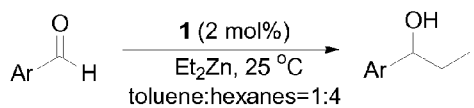

| entry | aldehyde | product | yield[a] (%) | ee (%) |
|---|---|---|---|---|
| 1 | PhCHO | 1-phenylpropanol | 99 | 95[b] |
| 2 | 4-MeO-cinnamaldehyde | corresponding alcohol | 99 | 96[c] |
| 3 | 3-MeO-C6H4-CHO | corresponding alcohol | 92 | 91[b] |
| 4 | 4-NC-C6H4-CHO | corresponding alcohol | 91 | 90[b] |
| 5 | 3-NC-C6H4-CHO | corresponding alcohol | 96 | 92[b] |
| 6 | 1-naphthaldehyde | corresponding alcohol | 87 | 78[b] |
| 7 | 2-naphthaldehyde | corresponding alcohol | 92 | 91[b] |
| 8 | 4-Me-C6H4-CHO | corresponding alcohol | 99 | 86[c] |
| 9 | 4-Cl-cinnamaldehyde | corresponding alcohol | 97 | 86[b] |
| 10 | 4-F-C6H4-CHO | corresponding alcohol | 95 | 94[b] |
| 11 | 3-thiophenecarboxaldehyde | corresponding alcohol | 99 | 71[b] |
| 12 | cyclohexanecarboxaldehyde | corresponding alcohol | 92 | 90[c] |

| Entry | Aldehyde | Product | Yield[a] (%) | ee (%) |
|---|---|---|---|---|
| 1 | PhCHO | Ph-CH(OH)Et | 92 | 88[b] |
| 2 | 2-naphthyl-CHO | 2-naphthyl-CH(OH)Et | 96 | 91[b] |
| 3 | 1-naphthyl-CHO | 1-naphthyl-CH(OH)Et | 86 | 92[b] |
| 4 | 4-NC-C6H4-CHO | 4-NC-C6H4-CH(OH)Et | 82 | 90[b] |
| 5 | 3-MeO-C6H4-CHO | 3-MeO-C6H4-CH(OH)Et | 87 | 82[b] |
| 6 | 4-F-C6H4-CHO | 4-F-C6H4-CH(OH)Et | 95 | 92[b] |
| 7 | 4-Br-C6H4-CHO | 4-Br-C6H4-CH(OH)Et | 93 | 89 |

Figure 6
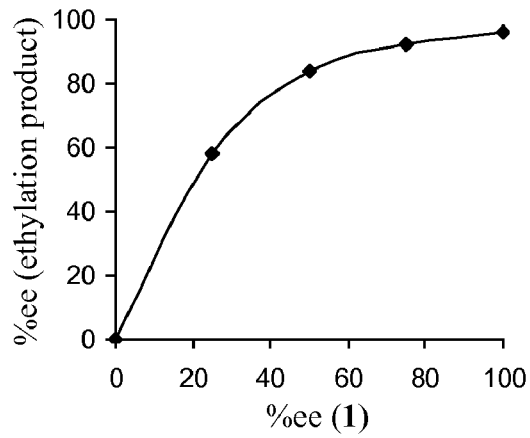
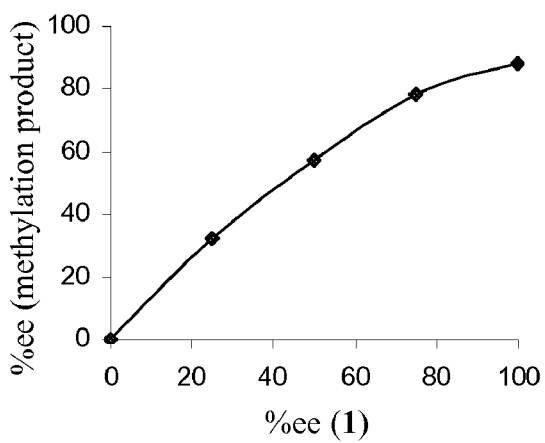
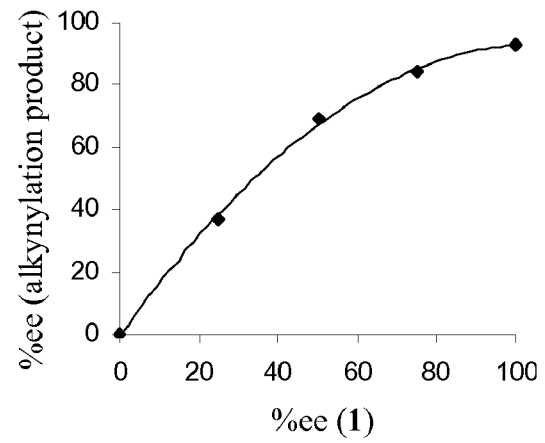

SYNTHESIS, STRUCTURE AND USE OF BISOXAZOLIDINES FOR ASYMMETRIC CATALYSIS AND SYNTHESIS

RELATED APPLICATIONS

This application claims the benefit of priority to U.S. provisional patent application Ser. Nos. 60/793,134, filed Apr. 19, 2006; which is hereby incorporated by reference in its entirety.

BACKGROUND

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. These advantages include the fewer side effects and greater potency often associated with enantiomerically pure compounds.

Traditional methods of organic synthesis were often optimized for the production of racemic materials. The production of enantiomerically pure material has historically been achieved in one of two ways: use of enantiomerically pure starting materials derived from natural sources (the so-called "chiral pool"); and the resolution of racemic mixtures by classical techniques. Each of these methods has serious drawbacks, however. The chiral pool is limited to compounds found in nature, so only certain structures and configurations are readily available. Resolution of racemates, which requires the use of resolving agents, may be inconvenient and time-consuming.

The ever-increasing industrial and academic demand for enantiopure chemicals has been accompanied by the development of numerous asymmetric synthetic methods utilizing highly efficient chiral catalysts and auxiliaries. For example, see: (a) Helmchen, G.; Hoffmann, R. W.; Mulzer, J.; Schaumann, E. (Eds.) Stereoselective Synthesis in Methods of Organic Chemistry, Houben-Weyl, Vol. 21, 4th edition., Thieme, Stuttgart, 1995; (b) Ojima, I. (Ed.) Catalytic Asymmetric Synthesis 2nd edition, Wiley-VCH, New York, 2000; (c) Noyori, R. *Angew. Chem. Int. Ed.* 2002, 41, 2008-2022; and (d) Sharpless, K. B. *Angew. Chem. Int. Ed.* 2002, 41, 2024-2032. Ideally, a practical asymmetric catalyst is inexpensive, readily available in both enantiopure forms, and provides high yields and enantioselectivities for a wide range of substrates in various reactions. Among the many chiral catalysts reported to date, a relatively small number derived from rigid $C_2$-symmetric ligands including BINOL, BOX, salen, DIOP, DUPHOS, and TADDOL have proved to be exceptionally versatile and effective.

Remarkably, as described herein, chiral catalysts derived from readily accessible rigid $C_2$-symmetric chiral bisoxazolidines, which can be derived from amino alcohols and diketones, have been developed. In addition, their successful use in asymmetric bond-forming reactions has been demonstrated.

SUMMARY

One aspect of the invention relates to chiral bisoxazolidines and their usefulness in asymmetric catalysis. The unique structure and the simplicity of preparation of chiral bisoxazolidines make them an attractive new class of compounds that is expected to find multiple applications, for example, in asymmetric synthesis. Another aspect of the invention relates to a method of preparing a bisoxazolidine catalyst, comprising the step of: reacting an amino alcohol with a diketone. In certain embodiments, the amino alcohol is a 1,2-amino alcohol or a 1,3-amino alcohol. In certain embodiments, the diketone is a cyclic 1,2-diketone.

Another aspect of the present invention relates to a method of preparing a chiral, non-racemic compound from an aldehyde, comprising the step of: reacting an aldehyde with a nucleophile in the presence of a catalyst; thereby producing a chiral, non-racemic compound; wherein said catalyst is a bisoxazolidine. For example, a bisoxazolidine ligand was successfully applied in the catalytic enantioselective alkynylation and alkylation of a range of aromatic and aliphatic aldehydes, generating chiral propargylic alcohols and secondary alcohols in high yields and enantiomeric excess.

BRIEF DESCRIPTION OF THE FIGURES

FIG. 1 depicts [A] a general bisoxazolidine structure, [B] synthesis and [C] single crystal structure of ligand 1.

FIG. 2 depicts examples of bisoxazolidine-catalyzed asymmetric alkynylation of aldehydes. Key: a—isolated yields; b—determined by HPLC on Chiralcel OD; c—at −15° C.; and d—obtained with recycled catalyst.

FIG. 3 depicts [A] structures of 3-silylpropargylic alcohols; and [B] a scheme showing an oxazolidine-catalyzed alkynylation.

FIG. 4 depicts examples of bisoxazolidine-catalyzed asymmetric ethylation of aldehydes. Key: a—isolated yields; b—determined by HPLC on Chiralcel OD, AD, OB-H; and c—determined by GC on octakis(6-O-methyl-2,3-di-O-pentyl)-γ-cyclodextrin.

FIG. 6 depicts graphs showing nonlinear effect in the catalytic enantioselective ethylation, methylation, and alkynylation (from top to bottom).

DETAILED DESCRIPTION

Figure 5:
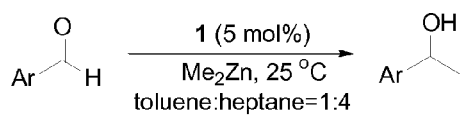
FIG. 5 depicts examples of bisoxazolidine-catalyzed asymmetric methylation of aldehydes. Key: a—isolated yields; and b—determined by HPLC on chiralcel AD.

Despite the structural similarity to bisoxazoline ligands which have been applied very successfully in catalytic asymmetric Diels-Alder and ene reactions, Mukaiyama aldol reactions, cyclopropanations, and aziridinations, to the best of our knowledge there have been no reports of asymmetric catalysts derived from bisoxazolidines. For example, see: (a) Evans, D. A.; Burgey, C. S.; Paras, N. A.; Vojkovsky, T.; Tregay, S. W. *J. Am. Chem. Soc.* 1998, 120, 5824-5825; (b) Evans, D. A.; Barnes, D. M.; Johnson, J. S.; Lectka, T.; Matt, P. V.; Miller, S. J.; Murry, J. A.; Norcross, R. D.; Shaughnessy, E. A.; Campos, K. J. *J. Am. Chem. Soc.* 1999, 121, 7582-7594; (c) Matsunaga, H.; Yamada, Y.; Tsukasa, I. *Tetrahedron: Asymm.* 1999, 10, 3095-3098; (d) Bedekar, A. V.; Koroleva, E. B.; Andersson, P. G. *J. Org. Chem.* 1997, 62, 2518-2526; and (e) Evans, D. A.; Faul, M. M.; Bilodeau, M. T.; Anderson, B. A.; Barnes, D. M. *J. Am. Chem. Soc.* 1993, 115, 5328-5329. In analogy to chiral bisoxazolines, which are easily synthesized from readily available amino alcohols and malonyl dichloride or derivatives thereof, we expected that bisoxazolidines could be prepared in a single step by replacing the diacyl halide with a 1,2-diketone. Herein, we report the first example of a chiral bisoxazolidine (FIG. 1A) and describe its use for catalytic asymmetric synthesis.

Definitions

For convenience, before further description of the present invention, certain terms employed in the specification, examples, and appended claims are collected here.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "nucleophile" is recognized in the art, and as used herein means a chemical moiety having a reactive pair of electrons.

The term "electrophile" is art-recognized and refers to chemical moieties which can accept a pair of electrons from a nucleophile as defined above. Electrophilic moieties useful in the method of the present invention include aldehydes.

The terms "electrophilic atom," "electrophilic center" and "reactive center" as used herein refer to the atom of the substrate aryl moiety which is attacked by, and forms a new bond to the nucleophilic heteroatom of the hydrazine and the like. In most (but not all) cases, this will also be the carbon of a carbonyl moiety.

The term "catalytic amount" is recognized in the art and means a substoichiometric amount of reagent relative to a reactant. As used herein, a catalytic amount means from 0.0001 to 90 mole percent reagent relative to a reactant, more preferably from 0.001 to 50 mole percent, still more preferably from 0.01 to 10 mole percent, and even more preferably from 0.1 to 5 mole percent reagent to reactant.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 80 or fewer carbon atoms in its backbone (e.g., $C_1$-$C_{80}$ for straight chain, $C_3$-$C_{80}$ for branched chain), and alternatively, about 30 or fewer. Likewise, cycloalkyls have from about 3 to about 10 carbon atoms in their ring structure, and alternatively about 5, 6 or 7 carbons in the ring structure. As used herein, "fluoroalkyl" denotes an alkyl where one or more hydrogens have been replaced with fluorines; "perfluoroalkyl" denotes an alkyl where all the hydrogens have been replaced with fluorines.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "alkylene," is art-recognized, and as used herein, pertains to a bidentate moiety obtained by removing two hydrogen atoms, either both from the same carbon atom, or one from each of two different carbon atoms, of a hydrocarbon compound, which may be aliphatic or alicyclic, or a combination thereof, and which may be saturated, partially unsaturated, or fully unsaturated.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, alkylthio, sulfonyl, sulfonamido, ketone, aldehyde, ester, heterocyclyl, aromatic or heteroaromatic moieties, trifluoromethyl, cyano, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, alkylthio, sulfonyl, ketone, aldehyde, ester, a heterocyclyl, an aromatic or heteroaromatic moiety, trifluoromethyl, cyano, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, alkylthio, sulfonyl, ketone, aldehyde, ester, a heterocyclyl, an aromatic or heteroaromatic moiety, trifluoromethyl, cyano, or the like.

The term "carbocycle" is art-recognized and refers to an aromatic or non-aromatic ring in which each atom of the ring is carbon.

The terms "monocyclic," "bicyclic," or "tricyclic" ring systems refers to 5 or 6 member monocyclic rings, 8, 9 and 10 membered bicyclic ring structures, and 11, 12, 13 and 14 membered tricyclic ring structures, wherein each bond in each ring may be possess any degree of saturation that is chemically feasible. When such structures contain substituents, those substituents may be at any position of the ring system, unless otherwise specified. As specified, such ring systems may optionally comprise up to 4 heteroatoms selected from N, O or S. Those heteroatoms may replace any carbon atoms in these ring systems as long as the resulting compound is chemically stable.

The term "monocyclic" ring system, as used herein, includes saturated, partially unsaturated and fully unsaturated ring structures. The term "bicyclic" ring system, as used herein, includes systems wherein each ring is independently saturated, partially unsaturated and fully unsaturated. Examples of monocyclic and bicyclic ring systems useful in the compounds of this invention include, but are not limited to, cyclopentane, cyclopentene, indane, indene, cyclohexane, cyclohexene, cyclohexadiene, benzene, tetrahydronaphthalene, decahydronaphthalene, naphthalene, pyridine, piperidine, pyridazine, pyrimidine, pyrazine, 1,2,3-triazine, 1,2,4-triazine, 1,3,5-triazine, 1,2,3,4-tetrazine, 1,2,4,5-tetrazine, 1,2,3,4-tetrahydroquinoline, quinoline, 1,2,3,4-tetrahydroisoquinoline, isoquinoline, cinnoline, phthalazine, quinazoline, quinoxaline, 1,5-naphthyridine, 1,6-naphthyridine, 1,7-naphthyridine, 1,8-naphthyridine, 2,6-naphthyridine, 2,7-naphthyridine, pteridine, acridine, phenazine, 1,10-phenatroline, dibenzopyrans, 1-benzopyrans, phenothiazine, phenoxazine, thianthrene, dibenzo-p-dioxin, phenoxathiin, phenoxthionine, morpholine, thiomorpholine, tetrahydropyan, pyran, benzopyran, 1,4-dioxane, 1,3-dioxane, dihyropyridine, dihydropyran, 1-pyrindine, quinuclidine, triazolopyridine, β-carboline, indolizine, quinolizidine, tetrahydronaphtheridine, diazaphenanthrenes, thiopyran, tetrahydrothiopyran, benzodioxane, furan, benzofuran, tetrahydrofuran, pyrrole, indole, thiophene, benzothiopene, carbazole, pyrrolidine, pyrazole, isoxazole, isothiazole, imidazole, oxazole, thiazole, 1,2,3-triazole, 1,2,4-triazole, 1,2,3-oxadiazole, 1,2,4-oxadiazole, 1,3,4 oxadiazole, 1,2,5-oxadiazole, 1,2,3-thiadiazole, 1,2,4-thiadiazole, 1,3,4-thiadiazole, 1,2,5 thiadiazole, tetrazole, benzothiazole, benzoxazole, benzotriazole, benzimidazole, benzopyrazole, benzisothiazole, benzisoxazole and purine.

Additional monocyclic and bicyclic structures falling within the above description may be found in A. R. Katritzky, and C. W. Rees, eds. "Comprehensive Heterocyclic Chemistry: Structure, Reactions, Synthesis and Use of Heterocyclic Compounds, Vol. 1-8," Pergamon Press, NY (1984), the disclosure of which is herein incorporated by reference.

It should be understood that heterocycles may be attached to the rest of the compound by any atom of the heterocycle which results in the creation of a stable structure.

The term "ring atom", as used herein, refers to a backbone atom that makes up the ring. Such ring atoms are selected from C, N, O or S and are bound to 2 or 3 other such ring atoms (3 in the case of certain ring atoms in a bicyclic ring system). The term "ring atom" does not include hydrogen.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2^-$. "Halide" designates the corresponding anion of the halogens, and "pseudohalide" has the definition set forth on page 560 of "Advanced Inorganic Chemistry" by Cotton and Wilkinson, that is, for example, monovalent anionic groups sufficiently electronegative to exhibit a positive Hammett sigma value at least equaling that of a halide (e.g., CN, OCN, SCN, SeCN, TeCN, $N_3$, and $C(CN)_3$).

The terms "amine" and "amino" are art-recognized and refer to both unsubstituted and substituted amines, e.g., a moiety that may be represented by the general formulas:

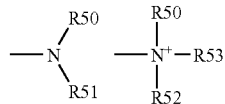

wherein R50, R51, R52 and R53 each independently represent a hydrogen, an alkyl, an alkenyl, —$(CH_2)_m$—R61, or R50 and R51 or R52, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

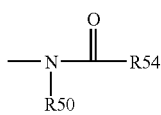

wherein R50 is as defined above, and R54 represents a hydrogen, an alkyl, an alkenyl or —$(CH_2)_m$—R61, where m and R61 are as defined above.

The term "amido" is art recognized as an amino-substituted carbonyl and includes a moiety that may be represented by the general formula:

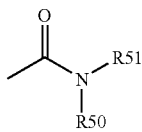

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "carboxyl" is art recognized and includes such moieties as may be represented by the general formulas:

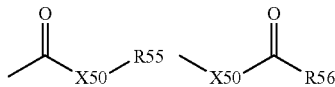

wherein X50 is a bond or represents an oxygen or a sulfur, and R55 and R56 represents a hydrogen, an alkyl, an alkenyl, —$(CH_2)_m$—R61 or a pharmaceutically acceptable salt, R56 represents a hydrogen, an alkyl, an alkenyl or —$(CH_2)_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularyl when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "oxime" and "oxime ether" are art-recognized and refer to moieties that may be represented by the general formula:

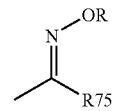

wherein R75 is hydrogen, alkyl, cycloalkyl, alkenyl, alkynyl, aryl, aralkyl, or —$(CH_2)_m$—R61. The moiety is an "oxime" when R is H; and it is an "oxime ether" when R is alkyl, cycloalkyl, alkenyl, alkynyl, aryl, aralkyl, or —$(CH_2)_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—$(CH_2)_m$—R61, where m and R61 are described above.

The term "sulfonate" is art recognized and refers to a moiety that may be represented by the general formula:

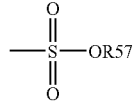

in which R57 is an electron pair, hydrogen, alkyl, cycloalkyl, or aryl.

The term "sulfate" is art recognized and includes a moiety that may be represented by the general formula:

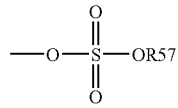

in which R57 is as defined above.

The term "sulfonamido" is art recognized and includes a moiety that may be represented by the general formula:

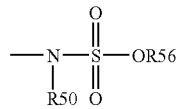

in which R50 and R56 are as defined above.

The term "sulfamoyl" is art-recognized and refers to a moiety that may be represented by the general formula:

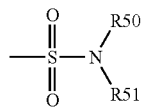

in which R50 and R51 are as defined above.

The term "sulfonyl" is art-recognized and refers to a moiety that may be represented by the general formula:

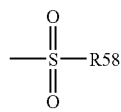

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

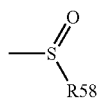

in which R58 is defined above.

The term "phosphoryl" is art-recognized and may in general be represented by the formula:

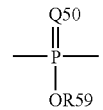

wherein Q50 represents S or O, and R59 represents hydrogen, a lower alkyl or an aryl. When used to substitute, e.g., an alkyl, the phosphoryl group of the phosphorylalkyl may be represented by the general formulas:

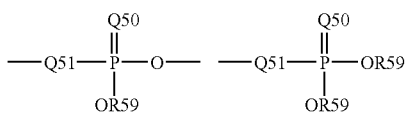

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

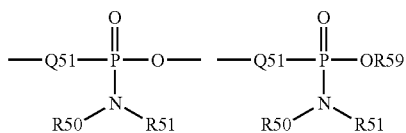

wherein Q51, R50, R51 and R59 are as defined above.

The term "phosphonamidite" is art-recognized and may be represented in the general formulas:

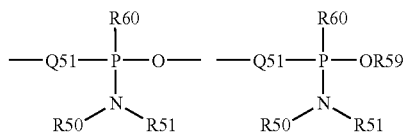

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The definition of each expression, e.g., alkyl, m, n, and the like, when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

The term "diketone" is intended to embrace all compounds containing two ketone carbonyl groups. An example of a simple aliphatic diketone is diacetyl-2,3-butadione. In certain embodiments, diketones are selected from the group consisting of 1,2-diketones (diacetyl for example), 1,3-diketones (acetylacetone, for example), and 1,4-diketones (hexane-2,5-dione, for example).

The term "amino alcohol" is intended to embrace all compounds, whether natural or synthetic, which include both an amino functionality and an alcohol functionality. In certain embodiments, the amino alcohols contemplated in the present invention are the reduced form of amino acids. The term "amino acid" is intended to embrace all compounds, whether natural or synthetic, which include both an amino functionality and an acid functionality, including amino acid analogues and derivatives.

In certain embodiments, the amino alcohols contemplated in the present invention are the reduced form of naturally occurring amino acids found in proteins, or the naturally occurring anabolic or catabolic products of such amino acids, which contain amino and carboxyl groups. Naturally occurring amino acids are identified throughout by the conventional three-letter and/or one-letter abbreviations, corresponding to the trivial name of the amino acid, in accordance with the following list: Alanine (Ala), Arginine (Arg), Asparagine (Asn), Aspartic acid (Asp), Cysteine (Cys), Glutamic acid (Glu), Glutamine (Gln), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr), and Valine (Val). The abbreviations are accepted in the peptide art and are recommended by the IUPAC-IUB commission in biochemical nomenclature.

In other embodiments, the amino alcohols contemplated in the present invention are the reduced form of non-natural amino acids. Examples of non-naturally occurring amino acids include, but are not limited to, D-amino acids (i.e. an amino acid of an opposite chirality to the naturally occurring form), N-α-methyl amino acids, C-α-methyl amino acids, β-methyl amino acids, β-alanine (β-Ala), norvaline (Nva), norleucine (Nle), 4-aminobutyric acid (γ-Abu), 2-aminoisobutyric acid (Aib), 6-aminohexanoic acid (ε-Ahx), ornithine (orn), hydroxyproline (Hyp), sarcosine, citrulline, cysteic acid, cyclohexylalanine, α-amino isobutyric acid, t-butylglycine, t-butylalanine, 3-aminopropionic acid, 2,3-diaminopropionic acid (2,3-diaP), D- or L-phenylglycine, D- or L-2-naphthylalanine (2-NaI), 1,2,3,4-tetrahydroisoquinoline-3-carboxylic acid (Tic), D- or L-2-thienylalanine (Thi), D- or L-3-thienylalanine, D- or L-1-, 2-, 3- or 4-pyrenylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylalanine, D- or L-p-methoxybiphenylalanine, methionine sulphoxide (MSO) and homoarginine (Har).

Other examples of non-naturally occurring amino acids include 3-(2-chlorophenyl)-alanine, 3-chloro-phenylalanine, 4-chloro-phenylalanine, 2-fluoro-phenylalanine, 3-fluoro-phenylalanine, 4-fluoro-phenylalanine, 2-bromo-phenylalanine, 3-bromo-phenylalanine, 4-bromo-phenylalanine, homophenylalanine, 2-methyl-phenylalanine, 3-methyl-phenylalanine, 4-methyl-phenylalanine, 2,4-dimethyl-phenylalanine, 2-nitro-phenylalanine, 3-nitro-phenylalanine, 4-nitro-phenylalanine, 2,4-dinitro-phenylalanine, 1,2,3,4-tetrahydroisoquinoline-3-carboxylic acid, 1,2,3,4-tetrahydronorharman-3-carboxylic acid, 1-naphthylalanine, 2-naphthylalanine, pentafluorophenylalanine, 2,4-dichloro-phenylalanine, 3,4-dichloro-phenylalanine, 3,4-difluoro-phenylalanine, 3,5-difluoro-phenylalanine, 2,4,5-trifluoro-phenylalanine, 2-trifluoromethyl-phenylalanine, 3-trifluoromethyl-phenylalanine, 4-trifluoromethyl-phenylalanine, 2-cyano-phenyalanine, 3-cyano-phenyalanine, 4-cyano-phenyalanine, 2-iodo-phenyalanine, 3-iodo-phenyalanine, 4-iodo-phenyalanine, 4-methoxyphenylalanine, 2-aminomethyl-phenylalanine, 3-aminomethyl-phenylalanine, 4-aminomethyl-phenylalanine, 2-carbamoyl-phenylalanine, 3-carbamoyl-phenylalanine, 4-carbamoyl-phenylalanine, m-tyrosine, 4-amino-phenylalanine, styrylalanine, 2-amino-5-phenyl-pentanoic acid, 9-anthrylalanine, 4-tert-butyl-phenylalanine, 3,3-diphenylalanine, 4,4'-diphenylalanine, benzoylphenylalanine, α-methyl-phenylalanine, α-methyl-4-fluoro-phenylalanine, 4-thiazolylalanine, 3-benzothienylalanine, 2-thienylalanine, 2-(5-bromothienyl)-alanine, 3-thienylalanine, 2-furylalanine, 2-pyridylalanine, 3-pyridylalanine, 4-pyridylalanine, 2,3-diaminopropionic acid, 2,4-diaminobutyric acid, allylglycine, 2-amino-4-bromo-4-pentenoic acid, propargylglycine, 4-aminocyclopent-2-enecarboxylic acid, 3-aminocyclopentanecarboxylic acid, 7-amino-heptanoic acid, dipropylglycine, pipecolic acid, azetidine-3-carboxylic acid, cyclopropylglycine, cyclopropylalanine, 2-methoxy-phenylglycine, 2-thienylglycine, 3-thienylglycine, trans-4-phenyl-pyrrolidine-3-carboxylic acid, trans-4-(2-fluoro-phenyl)-pyrrolidine-3-carboxylic acid, trans-4-(3-fluoro-phenyl)-pyrrolidine-3-carboxylic acid, trans-4-(4-fluoro-phenyl)-pyrrolidine-3-carboxylic acid, trans-4-(2-chloro-phenyl)-pyrrolidine-3-carboxylic acid, trans-4-(3-chloro-phenyl)-pyrrolidine-3-carboxylic acid, trans-4-(4-chloro-phenyl)-pyrrolidine-3-carboxylic acid, trans-4-(2-bromo-phenyl)-pyrrolidine-3-carboxylic acid, trans-4-(3-bromo-phenyl)-pyrrolidine-3-carboxylic acid, trans-4-(4-bromo-phenyl)-pyrrolidine-3-carboxylic acid, trans-4-(2-methyl-phenyl)-pyrrolidine-3-carboxylic acid, trans-4-(3-methyl-phenyl)-pyrrolidine-3-carboxylic acid, trans-4-(4-methyl-phenyl)-pyrrolidine-3-carboxylic acid, trans-4-(2-nitro-phenyl)-pyrrolidine-3-carboxylic acid, trans-4-(3-nitro-phenyl)-pyrrolidine-3-carboxylic acid, trans-4-(4-nitro-phenyl)-pyrrolidine-3-carboxylic acid, trans-4-(1-naphthyl)-pyrrolidine-3-carboxylic acid, trans-4-(2-naphthyl)-pyrrolidine-3-carboxylic acid, trans-4-(2,5-dichloro-phenyl)-pyrrolidine-3-carboxylic acid, trans-4-(2,3-dichloro-phenyl)-pyrrolidine-3-carboxylic acid, trans-4-(2-trifluoromethyl-phenyl)-pyrrolidine-3-carboxylic acid, trans-4-(3-trifluoromethyl-phenyl)-pyrrolidine-3-carboxylic acid, trans-4-(4-trifluoromethyl-phenyl)-pyrrolidine-3-carboxylic acid, trans-4-(2-cyano-phenyl)-pyrrolidine-3-carboxylic acid, trans-4-(3-cyano-phenyl)-pyrrolidine-3-carboxylic acid, trans-4-(4-cyano-phenyl)-pyrrolidine-3-carboxylic acid, trans-4-(2-methoxy-phenyl)-pyrrolidine-3-carboxylic acid, trans-4-(3-methoxy-phenyl)-pyrrolidine-3-carboxylic acid, trans-4-(4-methoxy-phenyl)-pyrrolidine-3-carboxylic acid, trans-4-(2-hydroxy-phenyl)-pyrrolidine-3- carboxylic acid, trans-4-(3-hydroxy-phenyl)-pyrrolidine-3-carboxylic acid, trans-4-(4-hydroxy-phenyl)-pyrrolidine-3-carboxylic acid, trans-4-(2,3-dimethoxy-phenyl)-pyrrolidine-3-carboxylic acid, trans-4-(3,4-dimethoxy-phenyl)-pyrrolidine-3-carboxylic acid, trans-4-(3,5-dimethoxy-phenyl)-pyrrolidine-3-carboxylic acid, trans-4-(2-pyridinyl)-pyrrolidine-3-carboxylic acid, trans-4-(3-pyridinyl)-pyrrolidine-3-carboxylic acid, trans-4-(6-methoxy-3-pyridinyl)-pyrrolidine-3-carboxylic acid, trans-4-(4-pyridinyl)-pyrrolidine-3-carboxylic acid, trans-4-(2-thienyl)-pyrrolidine-3-carboxylic acid, trans-4-(3-thienyl)-pyrrolidine-3-carboxylic acid, trans-4-(2-furanyl)-pyrrolidine-3-carboxylic acid, trans-4-isopropyl-pyrrolidine-3-carboxylic acid, 4-phosphonomethyl-phenylalanine, benzyl-phosphothreonine, (1'-amino-2-phenyl-ethyl)oxirane, (1'-amino-2-cyclohexyl-ethyl)oxirane, (1'-amino-2-[3-bromo-phenyl]ethyl)oxirane, (1'-amino-2-[4-(benzyloxy)phenyl]ethyl)oxirane, (1'-amino-2-[3,5-difluoro-phenyl]ethyl)oxirane, (1'-amino-2-[4-carbamoyl-phenyl]ethyl)oxirane, (1'-amino-2-[benzyloxy-ethyl])oxirane, (1'-amino-2-[4-nitro-phenyl]ethyl)oxirane, (1'-amino-3-phenyl-propyl)oxirane, (1'-amino-3-phenyl-propyl)oxirane, and/or salts and/or protecting group variants thereof.

Certain compounds of the present invention (such as the amino alcohols discussed above) may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, "Handbook of Chemistry and Physics", 67th Ed., 1986-87, inside cover.

While several embodiments of the present invention are described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

Bisoxazolidines of the Invention

In certain embodiments, a catalyst of the present invention is a bisoxazolidine. Not intending to limit the invention in any way, in certain embodiments the bisoxazolidine ligand may be formed by the reaction of at least two equivalents of an amino alcohol with one equivalent of a diketone.

While all types cyclic and acyclic diketones may be used, in certain embodiments the diketones are cyclic 1,2-diketones or cyclic 1,3-diketones. Such cyclic diketones, when combined with at least two equivalents of an amino alcohol, may form the following two classes of bisoxazolidine ligands (parent diketones are shown in brackets below):

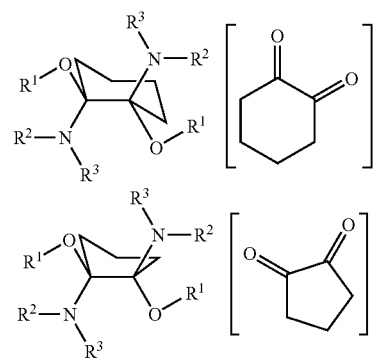

wherein the definitions of $R^1$, $R^2$ and $R^3$ are the same as those provided elsewhere herein. Importantly, the instant invention also encompasses bisoxazolidine ligands wherein the diketones are further substituted, or wherein the cyclic diketone is fused to another carbocyclic, heterocyclic, aromatic or heteroaromatic ring. As for the amino alcohol, in certain embodiments, it may be derived from a natural or non-natural amino acid via reduction of the acid moiety to an alcohol. Examples of natural and non-natural amino alcohols are provided elsewhere herein.

For example, employing (1R,2S)-cis-1-amino-2-indanol in the acid-promoted reaction with 1,2-cyclohexanedione, bisoxazolidine 1 was obtained in 90% yield and 99% de (FIG. 1B). It was shown that compound 1 was produced with excellent diastereoselectivity and exclusive formation of the (S,S)—N,O-diketal by crystallographic analysis: careful evaporation of a solution of 1 in chloroform gave the single crystal suitable for crystallographic analysis (CDCC602445). (Crystal structure data: $C_{24}H_{26}N_2O_2$, monoclinic, space group P21, a=16.9199(16) Å, b=5.5487(5) Å, c=23.585(2) Å, α=90.00°, β=108.5190(10)°, γ=90.00°, V=2099.6(3) Å$^3$, Z=4, $\rho_{calcd}$=1.367 g cm$^{-3}$, T=173 K.) It was shown that the ligand possesses a $C_2$-symmetric structure and an averaged separation of 2.35 Å between the nitrogen and oxygen atoms which facilitates bidentate binding to metal ions and organometallic compounds (FIG. 1C). It was envisioned that 1, as well as other bisoxazolidines, would be useful for a variety of asymmetric reactions.

One aspect of the present invention relates to a $C_2$-symmetric chiral bisoxazolidine of the present invention represented by formula I or formula II:

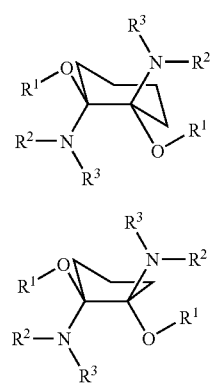

wherein, $R^1$ is alkyl, alkenyl, alkynyl, aryl, aralkyl, heteroaryl, heteroaralkyl, heterocyclic, or heterocycloalkyl;

$R^2$ is alkyl, alkenyl, alkynyl, aryl, aralkyl, heteroaryl, heteroaralkyl, heterocyclic, or heterocycloalkyl;

$R^3$ is hydrogen, alkyl, alkenyl, alkynyl, aryl, aralkyl, heteroaryl, heteroaralkyl, heterocyclic, or heterocycloalkyl;

any $R^1$ and $R^2$ taken together may represent a diradical, wherein said diradical, taken with the —O—C—N— fragment to which it is bound, forms a five- or six-membered heterocyclic moiety.

In certain embodiments, the present invention relates to the aforementioned bisoxazolidine and any of the attendant definitions, wherein the bisoxazolidine is represented by formula I.

In certain embodiments, the present invention relates to the aforementioned bisoxazolidine and any of the attendant definitions, wherein the bisoxazolidine is represented by formula II.

In certain embodiments, the present invention relates to the aforementioned bisoxazolidine and any of the attendant definitions, wherein $R^3$ is hydrogen.

In certain embodiments, the present invention relates to the aforementioned bisoxazolidine and any of the attendant definitions, wherein $R^1$ and $R^2$ taken together represent a diradical, thereby forming a bisoxazolidine of the present invention represented by formula III, formula IV, formula V or formula VI:

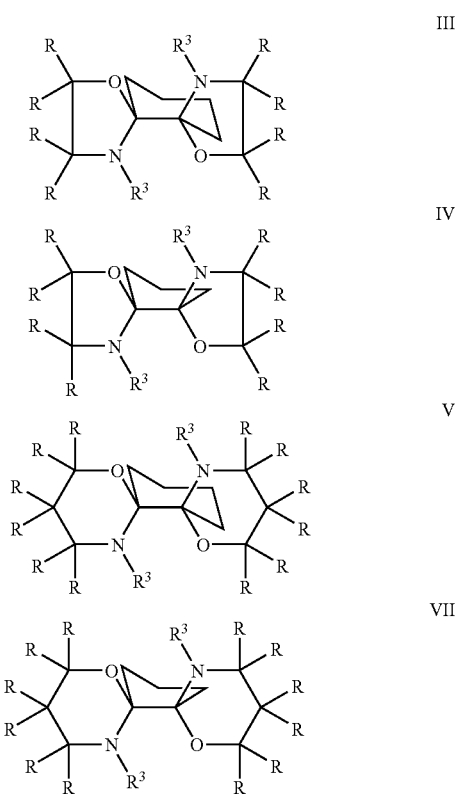

wherein,

R is, independently for each occurrence, hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, or ester; or any two adjacent R, taken together with the —C—C— fragment to which they are bound, is a carbocyclic moiety, a heterocyclic moiety, an aromatic moiety, or a heteroaromatic moiety; and $R^3$ is hydrogen, alkyl, alkenyl, alkynyl, aryl, aralkyl, heteroaryl, heteroaralkyl, heterocyclic, or heterocycloalkyl.

In certain embodiments, the present invention relates to the aforementioned bisoxazolidine and any of the attendant definitions, wherein the bisoxazolidine is represented by formula III.

In certain embodiments, the present invention relates to the aforementioned bisoxazolidine and any of the attendant definitions, wherein the bisoxazolidine is represented by formula IV.

In certain embodiments, the present invention relates to the aforementioned bisoxazolidine and any of the attendant definitions, wherein the bisoxazolidine is represented by formula V.

In certain embodiments, the present invention relates to the aforementioned bisoxazolidine and any of the attendant definitions, wherein the bisoxazolidine is represented by formula VI.

In certain embodiments, the present invention relates to the aforementioned bisoxazolidine and any of the attendant definitions, wherein R³ is hydrogen.

In certain embodiments, the present invention relates to the aforementioned bisoxazolidine and any of the attendant definitions, wherein R¹ and R² taken together represent a cyclic diradical, thereby forming a bisoxazolidine of the present invention represented by formula VII or formula VIII:

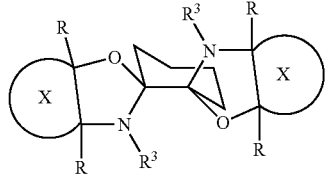

VII

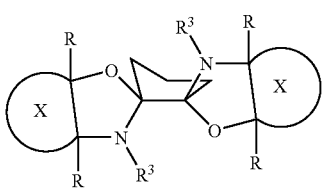

VIII wherein,

R is hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, or ester;

R³ is hydrogen, alkyl, alkenyl, alkynyl, aryl, aralkyl, heteroaryl, heteroaralkyl, heterocyclic, or heterocycloalkyl; and

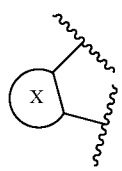

is a carbocyclic moiety, a heterocyclic moiety, an aromatic moiety, or a heteroaromatic moiety.

In certain embodiments, the present invention relates to the aforementioned bisoxazolidine and any of the attendant definitions, wherein the bisoxazolidine is represented by formula VII.

In certain embodiments, the present invention relates to the aforementioned bisoxazolidine and any of the attendant definitions, wherein the bisoxazolidine is represented by formula VIII.

In certain embodiments, the present invention relates to the aforementioned bisoxazolidine and any of the attendant definitions, wherein R³ is hydrogen.

In certain embodiments, the present invention relates to the aforementioned bisoxazolidine and any of the attendant definitions, wherein R is hydrogen or lower alkyl.

In certain embodiments, the present invention relates to the aforementioned bisoxazolidine and any of the attendant definitions, wherein R is hydrogen.

In certain embodiments, the present invention relates to the aforementioned bisoxazolidine and any of the attendant definitions, wherein

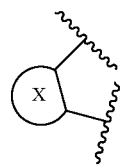

is a carbocyclic moiety, a heterocyclic moiety, an aromatic moiety, or a heteroaromatic moiety.

In certain embodiments, the present invention relates to the aforementioned bisoxazolidine and any of the attendant definitions, wherein

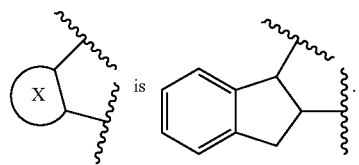

In certain embodiments, the present invention relates to the aforementioned bisoxazolidine and any of the attendant definitions, wherein R³ is hydrogen; and

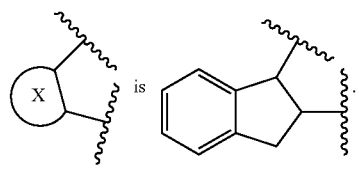

In certain embodiments, the present invention relates to the aforementioned bisoxazolidine and any of the attendant definitions, wherein R is hydrogen; R³ is hydrogen; and

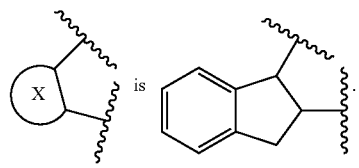

In certain embodiments, the present invention relates to the aforementioned bisoxazolidine and any of the attendant definitions, wherein the bisoxazolidine is represented by formula VII; R³ is hydrogen; and

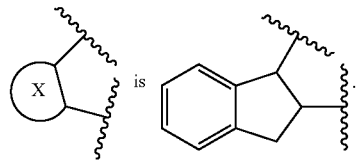

In certain embodiments, the present invention relates to the aforementioned bisoxazolidine and any of the attendant definitions, wherein the bisoxazolidine is

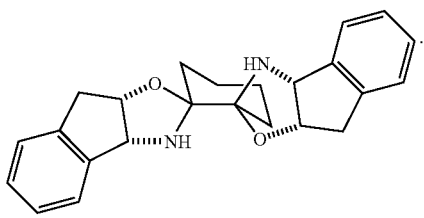

Reaction Conditions

The asymmetric reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely effect the substrate, the catalyst, or the product. For example, the reaction temperature influences the speed of the reaction, as well as the stability of the reactants, products, and catalyst. The reactions may be run at temperatures in the range of −78° C. to 100° C., or in the range −20° C. to 50° C., or in the range −20° C. to 25° C.

In general, the asymmetric synthesis reactions of the present invention are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents.

The invention also contemplates reaction in a biphasic mixture of solvents, in an emulsion or suspension, or reaction in a lipid vesicle or bilayer. In certain embodiments, it may be preferred to perform the catalyzed reactions in the solid phase.

In certain embodiments it is preferable to perform the reactions under an inert atmosphere of a gas such as nitrogen or argon.

The asymmetric synthesis processes of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral bisoxazoline can be immobilized or incorporated into a polymer or other insoluble matrix by, for example, covalently linking it to the polymer or solid support through one or more of its substituents. An immobilized chiral bisoxazoline may be easily recovered after the reaction, for instance, by filtration or centrifugation.

Catalyzed Reactions

In one aspect of the present invention there is provided a process for stereoselectively producing compounds with at least one stereogenic center from prochiral, or racemic starting materials using bisoxazolines. An advantage of this invention is that enantiomerically enriched products can be synthesized from prochiral or racemic reactants. Another advantage is that yield losses associated with the production of an undesired enantiomer can be substantially reduced or eliminated altogether.

In general, the invention features a stereoselective addition process which comprises combining a nucleophilic reactant, a prochiral or chiral substrate, and at least a catalytic amount of chiral bisoxazoline. Suitable substrates for the reaction include aldehydes susceptible to attack by the nucleophile. The combination of substrate, nucleophile, and bizoxazoline is maintained under conditions appropriate to catalyze the addition of the nucleophilic reactant to the aldehyde. This reaction can be applied to enantioselective processes as well as diastereoselective processes. It may also be adapted for regioselective reactions. In other words, enantioselective and diastereoselective reactions, kinetic resolutions, dynamic kinetic resolutions, and regioselective reactions all may be catalyzed according to the present invention.

Moreover, the methods of the invention can provide optically active products with very high stereoselectivity (e.g., enantioselectivity or diastereoselectivity) or regioselectivity. In preferred embodiments of the subject reactions, products with enantiomeric excess or diastereomeric excess of greater than about 50%, greater than about 70%, greater than about 90%, and greater than about 95% can be obtained. The methods of this invention may also be carried out under reaction conditions suitable for commercial use, and may proceed at reaction rates suitable for large scale operations.

In addition, the chiral products produced by the asymmetric synthesis processes of this invention can undergo further reaction(s) to afford desired derivatives thereof. Such permissible derivatization reactions can be carried out in accordance with conventional procedures known in the art. The invention expressly contemplates the preparation of end-products and synthetic intermediates which are useful for the preparation or development or both of therapeutic compounds.

One aspect of the present invention relates to a method of preparing a chiral, non-racemic compound from an aldehyde, comprising the step of:

reacting an aldehyde with a nucleophile in the presence of a catalyst; thereby producing a chiral, non-racemic compound; wherein said catalyst is a $C_2$-symmetric chiral bisoxazolidine.

Another aspect of the present invention relates to a method of preparing a chiral, non-racemic compound from an aldehyde, comprising the step of:

reacting an aldehyde with a nucleophile in the presence of a catalyst; thereby producing a chiral, non-racemic compound; wherein said catalyst is a $C_2$-symmetric chiral bisoxazolidine represented by formula I or formula II:

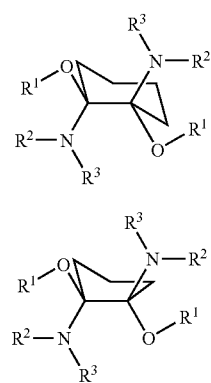

wherein, independently for each occurrence, $R^1$ is alkyl, alkenyl, alkynyl, aryl, aralkyl, heteroaryl, heteroaralkyl, heterocyclic, or heterocycloalkyl;

$R^2$ is alkyl, alkenyl, alkynyl, aryl, aralkyl, heteroaryl, heteroaralkyl, heterocyclic, or heterocycloalkyl;

$R^3$ is hydrogen, alkyl, alkenyl, alkynyl, aryl, aralkyl, heteroaryl, heteroaralkyl, heterocyclic, or heterocycloalkyl; and any $R^1$ and $R^2$ taken together may represent a diradical, wherein said diradical, taken with the —O—C—N— fragment to which it is bound, forms a five- or six-membered heterocyclic moiety; and the bisoxazolidine is a single stereoisomer.

In certain embodiments, the present invention relates to the aforementioned method and any of the attendant definitions, wherein the bisoxazolidine is represented by formula I.

In certain embodiments, the present invention relates to the aforementioned method and any of the attendant definitions, wherein the bisoxazolidine is represented by formula II.

In certain embodiments, the present invention relates to the aforementioned method and any of the attendant definitions, wherein $R^3$ is hydrogen.

In certain embodiments, the present invention relates to the aforementioned method and any of the attendant definitions, wherein $R^1$ and $R^2$ taken together represent a diradical so that said catalyst is a bisoxazolidine represented by formula III, formula IV, formula V or formula VII:

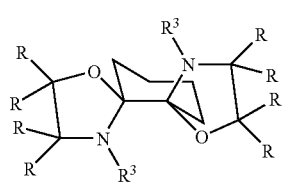

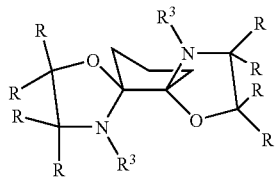

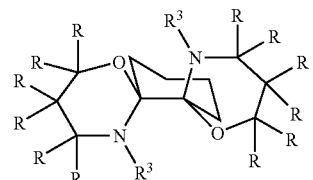

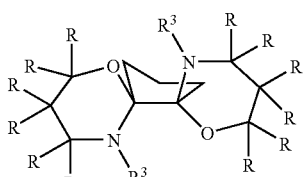

wherein, independently for each occurrence,

R is hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thio ether, sulfonyl, seleno ether, or ester; or any two adjacent R, taken together with the —C—C— fragment to which they are bound, is a carbocyclic moiety, a heterocyclic moiety, an aromatic moiety, or a heteroaromatic moiety; and $R^3$ is hydrogen, alkyl, alkenyl, alkynyl, aryl, aralkyl, heteroaryl, heteroaralkyl, heterocyclic, or heterocycloalkyl.

In certain embodiments, the present invention relates to the aforementioned method, wherein the bisoxazolidine is represented by formula III.

In certain embodiments, the present invention relates to the method, wherein the bisoxazolidine is represented by formula IV.

In certain embodiments, the present invention relates to the aforementioned method, wherein the bisoxazolidine is represented by formula V.

In certain embodiments, the present invention relates to the aforementioned method, wherein the bisoxazolidine is represented by formula VI.

In certain embodiments, the present invention relates to the aforementioned method and any of the attendant definitions, wherein $R^3$ is hydrogen.

In certain embodiments, the present invention relates to the aforementioned method and any of the attendant definitions, wherein $R^1$ and $R^2$ taken together represent a cyclic diradical so that said catalyst is a bisoxazolidine represented by formula VII or formula VIII:

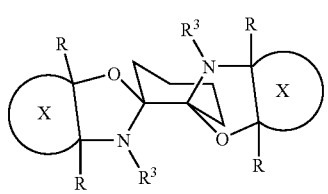

-continued

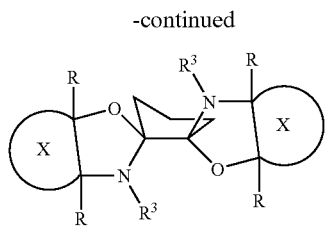

VIII wherein, independently for each occurrence,

R is hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, or ester;

$R^3$ is hydrogen, alkyl, alkenyl, alkynyl, aryl, aralkyl, heteroaryl, heteroaralkyl, heterocyclic, or heterocycloalkyl; and

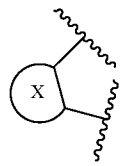

is a carbocyclic moiety, a heterocyclic moiety, an aromatic moiety, or a heteroaromatic moiety.

In certain embodiments, the present invention relates to the aforementioned method and any of the attendant definitions, wherein the bisoxazolidine is represented by formula VII.

In certain embodiments, the present invention relates to the aforementioned method and any of the attendant definitions, wherein the bisoxazolidine is represented by formula VIII.

In certain embodiments, the present invention relates to the aforementioned method and any of the attendant definitions, wherein $R^3$ is hydrogen.

In certain embodiments, the present invention relates to the aforementioned method and any of the attendant definitions, wherein R is hydrogen or lower alkyl.

In certain embodiments, the present invention relates to the aforementioned method and any of the attendant definitions, wherein R is hydrogen.

In certain embodiments, the present invention relates to the aforementioned method and any of the attendant definitions, wherein

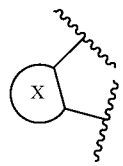

is a carbocyclic moiety, a heterocyclic moiety, an aromatic moiety, or a heteroaromatic moiety.

In certain embodiments, the present invention relates to the aforementioned method and any of the attendant definitions, wherein

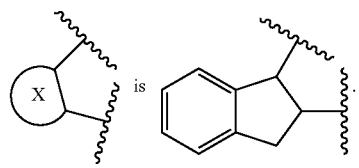

In certain embodiments, the present invention relates to the aforementioned method and any of the attendant definitions, wherein $R^3$ is hydrogen; and

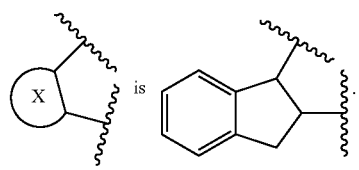

In certain embodiments, the present invention relates to the aforementioned method and any of the attendant definitions, wherein R is hydrogen; $R^3$ is hydrogen; and

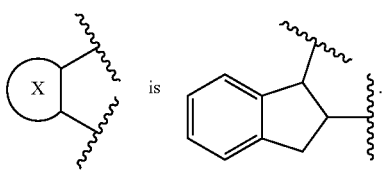

In certain embodiments, the present invention relates to the aforementioned method and any of the attendant definitions, wherein the bisoxazolidine is represented by formula VII; $R^3$ is hydrogen; and

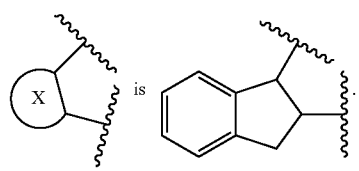

In certain embodiments, the present invention relates to the aforementioned method and any of the attendant definitions, wherein the bisoxazolidine is

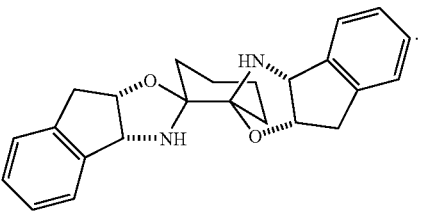

In certain embodiments, the present invention relates to the aforementioned method and any of the attendant definitions, wherein said aldehyde is an aromatic aldehyde.

In certain embodiments, the present invention relates to the aforementioned method and any of the attendant definitions, wherein said aldehyde is an aliphatic aldehyde.

In certain embodiments, the present invention relates to the aforementioned method and any of the attendant definitions, wherein said aldehyde is

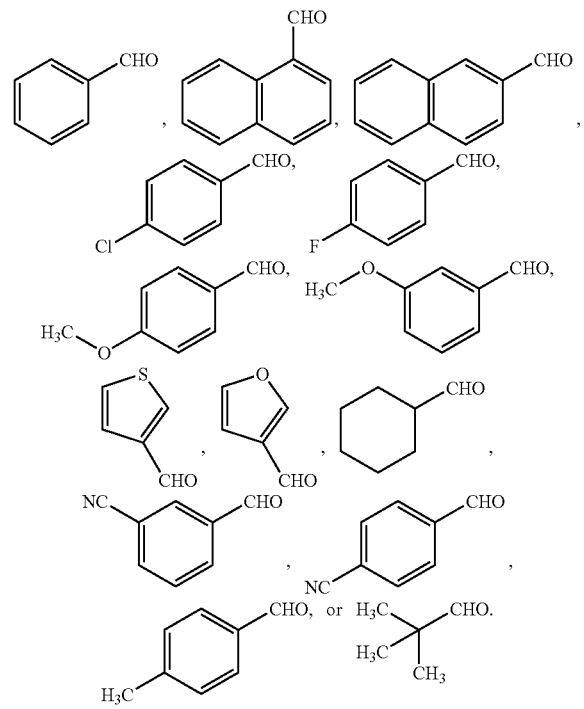

In certain embodiments, the present invention relates to the aforementioned method and any of the attendant definitions, wherein said nucleophile is formed from an acetylene and a dialkyl zinc.

In certain embodiments, the present invention relates to the aforementioned method and any of the attendant definitions, wherein said nucleophile is formed from an acetylene and a dimethyl zinc.

In certain embodiments, the present invention relates to the aforementioned method and any of the attendant definitions, wherein said nucleophile is formed from an acetylene and a diethyl zinc.

In certain embodiments, the present invention relates to the aforementioned method and any of the attendant definitions, wherein said acetylene is

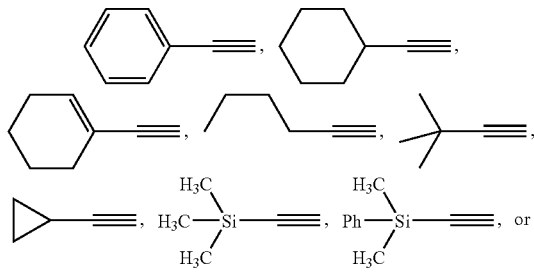

-continued

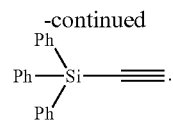

In certain embodiments, the present invention relates to the aforementioned method and any of the attendant definitions, wherein said nucleophile is formed from diethyl zinc.

In certain embodiments, the present invention relates to the aforementioned method and any of the attendant definitions, wherein said chiral, non-racemic compound is an alcohol.

In certain embodiments, the present invention relates to the aforementioned method and any of the attendant definitions, wherein said chiral, non-racemic compound is a propargylic alcohol.

In certain embodiments, the present invention relates to the aforementioned method and any of the attendant definitions, wherein said bisoxazolidine is present in less than about 70 mol % relative to said aldehyde.

In certain embodiments, the present invention relates to the aforementioned method and any of the attendant definitions, wherein said bisoxazolidine is present in less than about 40 mol % relative to said aldehyde.

In certain embodiments, the present invention relates to the aforementioned method and any of the attendant definitions, wherein said bisoxazolidine is present in less than about 10 mol % relative to said aldehyde.

In certain embodiments, the present invention relates to the aforementioned method and any of the attendant definitions, wherein said bisoxazolidine is present in less than about 5 mol % relative to said aldehyde.

In certain embodiments, the present invention relates to the aforementioned method and any of the attendant definitions, wherein said chiral, non-racemic compound has an enantiomeric excess greater than about 50%.

In certain embodiments, the present invention relates to the aforementioned method and any of the attendant definitions, wherein said chiral, non-racemic compound has an enantiomeric excess greater than about 70%.

In certain embodiments, the present invention relates to the aforementioned method and any of the attendant definitions, wherein said chiral, non-racemic compound has an enantiomeric excess greater than about 90%.

In certain embodiments, the present invention relates to the aforementioned method and any of the attendant definitions, wherein said chiral, non-racemic compound has an enantiomeric excess greater than about 95%.

Kinetic Resolutions

In another aspect of the present invention, a kinetic resolution of enantiomers or diastereomers of the substrate or the nucleophile is catalyzed by a bisoxazoline. For example, in the subject kinetic resolution processes for a racemic substrate, when the transformation is complete or interrupted one enantiomer can be preferentially recovered as unreacted substrate while the other has been preferentially transformed to the desired product. In other words, the kinetic resolution of the substrate can be performed to provide the desired enantiomer or diastereomer of the product. Of course, it will be appreciated that the kinetic resolution of the substrate can also be performed by removing the undesired enantiomer by reaction with a nucleophile, and recovering the desired enantiomer of the substrate unchanged from the reaction mixture. Likewise, the kinetic resolution of the nucleophile can be performed by removing the undesired enantiomer by reaction with a substrate, and recovering the desired enantiomer of the nucleophile unchanged from the reaction mixture. One significant advantage of kinetic resolutions is the ability to use inexpensive racemic starting materials rather than expensive, enantiomerically pure starting compounds.

In the non-dynamic kinetic resolution methods, as applied to a racemic substrate, one enantiomer can be recovered as unreacted substrate while the other is transformed to the desired product. Of course, one of ordinary skill in the art will recognize that the desired product of a kinetic resolution can be the enantiomer or diastereomer that reacts, the enantiomer or diastereomer that does not react, or both. One significant advantage of the methods of the present invention is the ability to use inexpensive racemic or diastereomeric mixtures of the starting materials, rather than expensive, enantiomerically or diastereomerically pure starting compounds.

The methods can also be applied to dynamic kinetic resolutions, e.g., wherein the yield of the enantiomerically or diastereomerically pure product from a kinetic resolution of a racemic substrate exceeds 50% due to in situ equilibration of the enantiomers or diastereomers of the substrate prior to the catalyzed attack of the nucleophile. Dynamic kinetic resolution methods are preferred for this reason.

In certain embodiments, the present invention relates to a method of performing a kinetic resolution of a racemic mixture or a diastereomeric mixture of a chiral substrate, comprising the step of combining a racemic mixture or a diastereomeric mixture of a chiral substrate with a nucleophile, in the presence of a chiral bisoxazoline, wherein said chiral bisoxazoline catalyzes the addition of said nucleophile to said chiral substrate to give a chiral product or unreacted chiral substrate or both enriched in one enantiomer or diastereomer. In certain embodiments, the present invention relates to the aforementioned method of performing a kinetic resolution, wherein said kinetic resolution is dynamic.

Asymmetric Catalysis and Synthesis

In certain embodiments the invention relates to enatioselective addition of organozinc reagents to aldehydes. Since chiral secondary alcohols have been identified as versatile building blocks for asymmetric synthesis, the enantioselective addition of organozinc reagents to aldehydes has emerged as one of the most important carbon-carbon bond forming reactions. Selected examples: (a) Tse, B. *J. Am. Chem. Soc.* 1996, 118, 7094-7100; (b) Marino Jr., J. P.; Overman, L. E. *J. Am. Chem. Soc.* 1999, 121, 5467-5480; (c) Trost, B. M.; Krische, M. J. *J. Am. Chem. Soc.* 1999, 121, 6131-6141; and (d) Sugiyama, H.; Yokokawa, F.; Shioiri, T. *Org. Lett.* 2000, 2, 2149-2152. To date, asymmetric alkynylation of aldehydes has been realized using stoichiometric amounts of chiral ligands and several catalytic procedures have been reported. Many of these protocols focus on the addition of phenylacetylene to aromatic aldehydes, while few address the need to utilize nonaromatic substrates. For example, see: (a) Corey, E. J.; Cimprich, K. A. *J. Am. Chem. Soc.* 1994, 116, 3151-3152; (b) Frantz, D. E.; Fässler, R.; Carreira, E. M. *J. Am. Chem. Soc.* 2000, 122, 1806-1807; (c) Cozzi, P. G.; Hilgraf, R.; Zimmermann, N. *Eur. J. Org. Chem.* 2004, 4095-4105. (d) Emmerson, D. P. G.; Hems, W. P.; Davis, B. G. *Org. Lett.* 2006, 8, 207-210; (e) Anand, N. K.; Carreira, E. M. *J. Am. Chem. Soc.* 2001, 123, 9687-9688; (f) Xu, Z.; Chen, C.; Xu, J.; Miao, M.; Yan, W.; Wang, R. *Org. Lett.* 2004, 6, 1193-1195; (g) Yamashita, M.; Yamada, K.; Tomioka, K. *Adv. Synth. Catal.* 2005, 347, 1649-1652; (h) Moore, D.; Pu, L. *Org. Lett.* 2002, 4, 1855-1857; (i) Li, X.; Lu, G.; Kwok, W. H.; Chan, A. S. C. *J. Am. Chem. Soc.* 2002, 124, 12636-12637; (j) Gao, G.; Xie, R.-G.; Pu, L.; *Proc. Natl. Acad. Sci. U.S.A.* 2004, 15, 5417-5420; (k) Ni, M.; Wang, R.; Han, Z.; Mao, B.; Da, C.; Liu, L.; Chen, C. *Adv. Synth. Catal.* 2005, 347, 1659-1665; (l) Takita, R.; Yakura, K.; Ohshima, T.; Shibasaki, M. *J. Am. Chem. Soc.* 2005, 127, 13760-13761; (m) Trost, B. M.; Weiss, A. H.; von Wangelin, A. J. *J. Am. Chem. Soc.* 2006, 128, 8-9; and (n) Gao, G.; Wang, Q.; Yu, X.-Q.; Xie, R.-G.; Pu, L. *Angew. Chem. Int. Ed.* 2006, 45, 122-125. It is therefore desirable to further extend this reaction to both aliphatic aldehydes and aliphatic alkynes. General drawbacks of currently existing methods include the need for freshly distilled solvents and purified reagents in addition to laborious and time-consuming procedures requiring stepwise premixing of chiral ligand, organozinc reagent, and acetylene in a certain order and stirring for extensive times, in some cases several hours, prior to the addition of the aldehyde.

Initial studies using various amounts of diethylzinc, phenylacetylene, and benzaldehyde in the presence of 10 mol % of 1 revealed that superior results can be obtained with nonpolar solvents such as hexanes and toluene while both yields and ee's dropped when tetrahydrofuran, diethyl ether or dichloromethane were used as solvent. We then varied the amount and ratio of both phenylacetylene and organozinc reagent and explored the use of diisopropyl- and dimethylzinc. To our delight, we found that the latter effectively impedes the competing alkylation reaction favoring alkynylation when equimolar amounts of dimethylzinc and phenylacetylene were employed in nonpolar solvents. Temperature and solvent composition proved to have a distinctive effect on yields and ee's and were carefully optimized. Best results were obtained using 10 mol % of 1 in a heptane-toluene mixture (5.6:1 v/v) at −4° C. For example, see Exemplification below.

Having optimized the bisoxazolidine-catalyzed alkynylation of benzaldehyde with phenylacetylene, we decided to screen a series of aromatic and aliphatic aldehydes and acetylenes to evaluate the scope of this reaction (FIG. 2). We were pleased to find that alkynylation of electron-rich and electron-deficient aromatic aldehydes with phenylacetylene in the presence of 10 mol % of 1 gave the corresponding propargylic alcohols in excellent yield and ee's (FIG. 2, entries 1-9). Importantly, our method is also suitable to both linear and branched aliphatic alkynes (FIG. 2, entries 10-14). For example, alkynylation of benzaldehyde with cyclohexylacetylene, and 1-hexyne proceeded with 87-96% yield and 92% ee. Excellent results were also observed with 1-ethynylcyclohexene and cyclopropylacetylene (FIG. 2, entries 12 and 14) which compare favorably to the 74-77% yield and 83-89% ee obtained with 10 mol % of an In(III)/BINOL catalyst. For example, see: Takita, R.; Yakura, K.; Ohshima, T.; Shibasaki, M. *J. Am. Chem. Soc.* 2005, 127, 13760-13761. Similarly, alkynylation of aliphatic aldehydes gave the corresponding propargylic alcohols in high yields and enantioselectivities (entries 15 and 16). Noteworthy, the catalyst has been recovered after asymmetric alkynylation of benzaldehyde with phenylacetylene and successfully recycled (FIG. 2, entry 1).

Catalyst 1 was also employed in the asymmetric addition of silylacetylenes to aldehydes under the same conditions. The corresponding 3-silylpropargylic alcohols were obtained in up to 88% yield and 99% ee (FIG. 3A). The efficient asymmetric synthesis of these compounds is important due to the versatile use of desilylated derivatives in alkylations and Sonogashira couplings. Noteworthy, our procedure eliminates the need for commonly used additives such as HMPA or titanium tetraisopropoxide while premixing and stirring of the ligand and the organozinc reagent or acetylene prior to addition of the aldehyde is not required. It should be noted, however, that various other procedures avoid cumbersome premixing and require only small amounts of inexpensive amine additives. For example, see: Li, Z.; Upadhyay, V.; DeCamp, A. E.; DiMichele, L.; Reider, P. J. *Synthesis* 1999, 1453-1458.

Although mono-oxazolidines have been used for alkylation and alkynylation of aldehydes, the $C_2$-symmetry of bisoxazolidine 1 provides superior results and appears to be crucial for both catalytic activity and asymmetric induction. For example, see: (a) Prasad, K. R. K.; Joshi, N. N. *J. Org. Chem.* 1997, 62, 3770-3771; (b) Kang, Y.; Wang, R.; Liu, L.; Da, C.; Yan, W.; Xu, Z. *Tetrahedron Lett.* 2005, 46, 863-865; and (c) Kang, Y. F.; Liu, L.; Wang, R.; Zhou, Y.-F. Yan, W. *J. Adv. Synth. Catal.* 2005, 347, 243-247. For comparison, we prepared a (1R,2S)-cis-1-amino-2-indanol-derived oxazolidine 2 using cyclohexanone instead of cyclohexanedione and tested its catalytic performance under the same reaction conditions. Alkynylation of benzaldehyde with phenylacetylene in the presence of 10 mol % of 2 gave the corresponding alcohol in only 76% yield and 17% ee (FIG. 3B).

Encouraged by the high yields and enantiomeric excess of propargylic alcohols obtained by bisoxazolidine-catalyzed alkynylation of aldehydes, we decided to employ 1 in the reaction of diethylzinc with various aldehydes (FIG. 4). Optimization of catalyst loading and solvents showed that the reaction proceeds in the presence of 2 mol % of bisoxazolidine 1 using hexanes and toluene (4:1 v/v) as solvent at room temperature. We were pleased to find that this procedure is suitable to aromatic and aliphatic aldehydes and provides the corresponding chiral alcohols in up to 99% yield and 96% ee. The catalyst is also suitable for methylation of aldehydes (see FIG. 5).

Nonlinear Effects

Bisoxazolidine 1 shows a positive nonlinear effect (NLE) as a result of inherently low solubility of the racemate in apolar organic solvents (FIG. 6). Racemic 1 forms a thermodynamically more stable crystal lattice and is significantly less soluble than the enantiopure ligand. This unexpected solid-liquid phase behavior increases the enantiomeric purity of scalemic 1 in solution and gives rise to a (+)-NLE that can not be described by Kagan's $ML_n$ model. For example, see: (a) Puchot, C.; Samuel, O.; Dunach, E.; Zhao, S.; Agami, C.; Kagan, H. B. *J. Am. Chem. Soc.* 1986, 108, 2353-2357; and (b) Girard, C.; Kagan, H. B. *Angew. Chem. Int. Ed.* 1998, 37, 2922-2959. The origin of nonlinearity is therefore attributed to thermodynamically controlled crystallization of racemic 1 leaving only the major enantiomer in solution and available for asymmetric catalysis.

EXEMPLIFICATION

The invention now being generally described, it will be more readily understood by reference to the following examples which are included merely for purposes of illustration of certain aspects and embodiments of the present invention, and are not intended to limit the invention.

Example 1

Synthesis and Characterization of 1

A mixture of cis-(1R,2S)-1-aminoindan-2-ol (5.0 g, 33.6 mmol) and 1,2-cyclohexanedione (1.8 g, 16.3 mmol) was refluxed in toluene using a Dean-Stark trap in the presence of catalytic amounts of formic acid until no water was formed. After cooling to room temperature, the solvent was removed under reduced pressure. The crude residue was dissolved in small amounts of dichloromethane and purified by crystallization upon addition of acetonitrile. Three crystallizations gave 5.5 g (14.5 mmol, 90%) of the product as a white powder. $^1$H NMR (300 MHz, CDCl$_3$) δ=0.87 (d, J=12.0 Hz, 2H), 1.26-1.46 (m, 6H), 2.83 (bs, 2H), 3.13 (d, J=2.9 Hz, 4H), 4.69-4.74 (m, 2H), 5.01 (d, J=5.3 Hz, 2H), 7.17-7.26 (m, 6H), 7.37-7.43 (m, 2H). $^{13}$C NMR (75 MHz, CDCl$_3$) δ=23.9, 37.2, 39.6, 69.9, 81.9, 102.1, 125.9, 126.0, 127.7, 128.6, 141.8, 144.6. Anal. Calcd $C_{24}H_{26}N_2O_2$: C, 76.98; H, 7.00; N, 7.48. Found: C, 76.66; H, 6.86; N, 7.40.

Example 2

Crystallographic Analysis of 1

Careful evaporation of a solution of 1 in chloroform gave a single crystal suitable for crystallographic analysis (CDCC602445). Crystal structure data: $C_{24}H_{26}N_2O_2$, monoclinic, space group P2$_1$, a=16.9199(16) Å, b=5.5487(5) Å, c=23.585(2) Å, α=90.00°, β=108.5190(10)°, γ=90.00°, V=2099.6(3) Å$^3$, Z=4, ρ$_{calcd}$=1.367 g cm$^{-3}$, T=173 K. Single crystal X-ray diffractions were performed at –100° C. using a Siemens platform diffractometer with graphite monochromated Mo-Kα radiation (λ=0.71073 Å). Data were integrated with the Siemens SAINT program and corrected for the affects of absorption using SADABS. The structures were solved by direct methods and refined with full-matrix least square analysis using SHELX-97-2 software. Non-hydrogen atoms were refined with anisotropic displacement parameters and all hydrogen atoms were placed in calculated positions and refined with a riding model.

Example 3

Synthesis of (1R,2S)-cis-1-Amino-2-indanol-derived oxazolidine

A mixture of (1R,2S)-1-aminoindan-2-ol (150 mg, 1 mmol) and cyclohexanone (98 mg, 1 mmol) was stirred in CH$_2$Cl$_2$ in the presence of molecular sieve (4 Å) for 17 h. Filtration and removal of the solvent under reduced pressure gave a colorless oil (220 mg, 96%). $^1$H NMR (300 MHz, CDCl$_3$) δ=1.35-1.74 (m, 10H), 2.38 (bs, 1H), 3.06 (dd, J=1.2 Hz, 18.8 Hz, 1H), 3.23 (dd, J=6.4 Hz, 18.8 Hz, 1H), 4.81 (ddd, J=1.2 Hz, 6.4 Hz, 6.4 Hz, 1H), 4.87 (d, J=6.4 Hz, 1H), 7.18-7.26 (m, 3H), 7.38 (m, 1H). $^{13}$C NMR (75 MHz, CDCl$_3$) δ=22.6, 22.9, 24.4, 34.3, 36.4, 38.2, 67.2, 78.5, 97.1, 124.2, 124.5, 126.1, 127.3, 140.5, 142.0. Anal. Calcd $C_{15}H_{19}$NO: C, 78.56; H, 8.35; N, 6.11. Found: C, 78.42; H, 8.32; N, 6.13.

Example 4

Enantioselective Alkynylation Procedure

Anhydrous solvents and reagents were commercially available and used without further purification. The alkyne (2.8 mmol) was added to a mixture of 1 (35 mg, 0.094 mmol, 10 mol %) and Me$_2$Zn (2.8 mmol, 1 M in heptane) in a solution of 2.8 ml of heptane and 0.5 ml of toluene at –4.0° C. After 10 minutes, 0.94 mmol of the aldehyde was added. Upon completion of the reaction (28 to 48 h), the mixture was treated with saturated NH$_4$Cl solution and extracted with CH$_2$Cl$_2$. The combined organic layers were dried over anhydrous MgSO$_4$ and solvents were removed under reduced pressure. Flash chromatography (SiO$_2$, particle size 32-63 μm, 5-15% of ethyl acetate in hexanes) afforded the pure propargylic alcohols. The enantiomeric excess was determined by HPLC (Chiralcel OD, 8% of EtOH in hexanes if not stated otherwise).

1-(1-Naphthyl)-3-phenyl-prop-2-yn-1-ol (Pu, L.; Moore, D. *Org. Lett.* 2002, 4, 1855-1857). $^1$H NMR (300 MHz, CDCl$_3$) δ=2.91 (d, J=5.1 Hz, 1H), 6.19 (d, J=5.1 Hz, 1H), 7.06-7.11 (m, 3H), 7.22-7.45 (m, 5H), 7.72-7.82 (m, 3H), 8.24 (d, J=7.8 Hz, 1H). $^{13}$C NMR (75 MHz, CDCl$_3$) δ=63.8, 87.8, 89.3, 123.1, 124.6, 125.2, 125.8, 126.4, 127.0, 128.8, 129.1, 129.3, 129.9, 131.1, 132.3, 134.6, 136.2.

1-(2-Naphthyl)-3-phenyl-prop-2-yn-1-ol (Pu, L.; Moore, D. *Org. Lett.* 2002, 4, 1855-1857). $^1$H NMR (300 MHz, CDCl$_3$) δ=2.54 (d, J=6.1 Hz, 1H), 6.19 (d, J=6.1 Hz, 1H), 7.30-7.33 (m, 3H), 7.44-7.51 (m, 4H), 7.69 (dd, J=1.7 Hz, 8.6 Hz, 1H), 7.81-7.87 (m, 3H), 8.02 (s, 1H). $^{13}$C NMR (75 MHz, CDCl$_3$) δ=65.8, 87.5, 89.4, 123.0, 125.3, 126.1, 126.8, 126.9, 128.3, 128.8, 128.9, 129.2, 129.3, 132.4, 133.8, 133.9, 138.6.

1-(3-Furyl)-3-phenyl-prop-2-yn-1-ol (Takita, R.; Yakura, K.; Ohshima, T.; Shibasaki, M. *J. Am. Chem. Soc.* 2005, 127, 13760-13761). $^1$H NMR (300 MHz, CDCl$_3$) δ=3.02 (bs, 1H), 5.60 (s, 1H), 6.54 (m, 1H), 7.25-7.31 (m, 3H), 7.37 (dd, J=2.0 Hz, 2.0 Hz, 1H), 7.42-7.45 (m, 2H), 7.55 (m, 1H). $^{13}$C NMR (75 MHz, CDCl$_3$) δ=58.2, 85.6, 88.9, 109.8, 122.8, 127.0, 128.9, 129.2, 132.3, 140.8, 144.2.

1-(3-Methoxyphenyl)-3-phenyl-prop-2-yn-1-ol (Pu, L.; Moore, D. *Org. Lett.* 2002, 4, 1855-1857). $^1$H NMR (300 MHz, CDCl$_3$) δ=3.03 (d, J=4.9 Hz, 1H), 3.75 (s, 3H), 5.62 (d, J=4.9 Hz, 1H), 6.82 (m, 1H), 7.14-7.17 (m, 2H), 7.23-7.29 (m, 4H), 7.41-7.44 (m, 2H). $^{13}$C NMR (75 MHz, CDCl$_3$) δ=55.8, 65.4, 87.0, 89.4, 112.7, 114.6, 119.6, 123.0, 128.9, 129.1, 130.2, 132.3, 142.8, 160.3.

1-(3-Thiophene)-3-phenyl-prop-2-yn-1-ol (Takita, R.; Yakura, K.; Ohshima, T.; Shibasaki, M. *J. Am. Chem. Soc.* 2005, 127, 13760-13761). $^1$H NMR (300 MHz, CDCl$_3$) δ=3.0 (bs, 1H), 5.67 (s, 1H), 7.21-7.29 (m, 5H), 7.40-7.45 (m, 3H). $^{13}$C NMR (75 MHz, CDCl$_3$) δ=61.5, 86.3, 89.3, 122.9, 123.3, 127.0, 127.1, 128.9, 129.2, 132.3, 142.6.

1-(4-Chlorophenyl)-3-phenyl-prop-2-yn-1-ol (Pu, L.; Moore, D. *Org. Lett.* 2002, 4, 1855-1857). $^1$H NMR (300 MHz, CDCl3) δ=2.98 (bs, 1H), 5.61 (s, 1H), 7.27-7.33 (m, 5H), 7.41-7.44 (m, 2H), 7.46-7.50 (m, 2H). $^{13}$C NMR (75 MHz, CDCl$_3$) δ=64.9, 87.5, 88.9, 122.7, 128.7, 128.9, 129.3, 129.4, 132.4, 134.8, 139.7.

1-(4-Fluorophenyl)-3-phenyl-prop-2-yn-1-ol (Takita, R.; Yakura, K.; Ohshima, T.; Shibasaki, M. *J. Am. Chem. Soc.* 2005, 127, 13760-13761). $^1$H NMR (300 MHz, CDCl$_3$) δ=3.07 (bs, 1H), 5.62 (s, 1H), 6.99-7.05 (m, 2H), 7.25-7.31 (m, 3H), 7.42-7.45 (m, 2H), 7.51-7.55 (m, 2H). $^{13}$C NMR (75 MHz, CDCl$_3$) δ=64.9, 87.4, 89.2, 115.7 (d, $J_{C,F}$=21.7 Hz), 122.5, 128.7, 128.9, 129.0 (d, $J_{C,F}$=5.0 Hz), 132.1, 136.8 (d, $J_{C,F}$=3.0 Hz), 163.0 (d, $J_{C,F}$=246.8 Hz).

1-Phenyl-3-cyclohexyl-prop-2-yn-1-ol (Niwa, S.; Soai, K. *J. Chem. Soc., Perkin Trans.* 1 1990, 937-943). $^1$H NMR (300 MHz, CDCl$_3$) δ=1.25-1.32 (m, 3H), 1.43-1.50 (m, 3H), 1.66-1.70 (m, 2H), 1.77-1.82 (m, 2H), 2.40 (m, 1H), 2.80 (d, J=5.9 Hz, 1H), 5.39 (d, J=5.9 Hz, 1H), 7.23-7.35 (m, 3H), 7.48-7.52 (m, 2H). $^{13}$C NMR (75 MHz, CDCl$_3$) δ=25.4, 26.4, 29.6, 33.1, 65.1, 80.5, 92.0, 127.2, 128.5, 128.9, 141.9.

1,3-Diphenyl-prop-2-yn-1-ol (Takita, R.; Yakura, K.; Ohshima, T.; Shibasaki, M. *J. Am. Chem. Soc.* 2005, 127, 13760-13761). $^1$H NMR (300 MHz, CDCl$_3$) δ=2.84 (bs, 1H), 5.64 (s, 1H), 7.25-7.42 (m, 6H), 7.43-7.45 (m, 2H), 7.56-7.59 (m, 2H). $^{13}$C NMR (75 MHz, CDCl$_3$) δ=65.6, 87.2, 89.4, 123.0, 127.4, 128.9, 129.0, 129.2, 129.3, 132.3, 141.2.

1-Phenyl-3-(1-cyclohexenyl)-prop-2-yn-1-ol (Takita, R.; Yakura, K.; Ohshima, T.; Shibasaki, M. *J. Am. Chem. Soc.* 2005, 127, 13760-13761). $^1$H NMR (300 MHz, CDCl$_3$) δ=1.54-1.73 (m, 4H), 2.09-2.29 (m, 4H), 5.57 (s, 1H), 6.16 (m, 1H), 7.26-7.41 (m, 3H), 7.48-7.57 (m, 2H). $^{13}$C NMR (75 MHz, CDCl$_3$) δ=22.0, 22.8, 26.2, 30.0, 65.5, 86.7, 89.1, 120.6, 127.3, 128.8, 129.1, 136.2, 141.6.

1-Phenyl-3-cyclopropyl-prop-2-yn-1-ol (Takita, R.; Yakura, K.; Ohshima, T.; Shibasaki, M. *J. Am. Chem. Soc.* 2005, 127, 13760-13761). $^1$H NMR (300 MHz, CDCl$_3$) δ=0.69-0.80 (m, 4H), 1.27 (m, 1H), 2.61 (bs, 1H), 5.36 (s, 1H), 7.27-7.36 (m, 3H), 7.46-7.50 (m, 2H). $^{13}$C NMR (75 MHz, CDCl$_3$) δ=-0.1, 8.9, 65.2, 75.8, 91.1, 127.2, 128.7, 129.0, 141.8.

1-Phenyl-hept-2-yn-1-ol (Braga, A. L.; Appelt, H. R.; Silveira, C. C.; Wessjohann, L. A.; Schneider, P. H. *Tetrahedron* 2002, 58, 10413-10416). $^1$H NMR (300 MHz, CDCl$_3$) δ=0.91 (t, J=7.3 Hz, 3H), 1.38-1.58 (m, 4H), 2.25 (dt, J=2.0 Hz, 6.8 Hz, 2H), 2.42 (d, J=5.1 Hz, 1H), 5.40 (s, 1H), 7.29-7.35 (m, 3H), 7.50-7.53 (m, 2H). $^{13}$C NMR (75 MHz, CDCl$_3$) δ=14.2, 19.1, 22.6, 31.2, 65.3, 80.6, 88.2, 127.2, 128.7, 129.1, 141.9.

4,4-Dimethyl-1-phenyl-pent-2-yn-1-ol (5). $^1$H NMR (300 MHz, CDCl$_3$) δ=1.25 (s, 9H), 2.40 (bs, 1H), 5.41 (d, J=5.4 Hz, 1H), 7.27-7.38 (m, 3H), 7.51-7.54 (m, 2H). $^{13}$C NMR (75 MHz, CDCl$_3$) δ=26.4, 29.9, 63.5, 77.4, 94.6, 125.7, 127.0, 127.4, 140.3.

1-(4-Methoxyphenyl)-3-phenyl-prop-2-yn-1-ol (Jiang, B.; Si, Y. *Tetrahedron Lett.* 2002, 43, 8323-8325). $^1$H NMR (300 MHz, CDCl$_3$) δ=2.18 (d, J=6.3 Hz, 1H), 3.83 (s, 3H), 5.64 (d, J=6.3 Hz, 1H), 6.93 (dd, J=2.2 Hz, 6.6 Hz, 2H), 7.92-7.95 (m, 3H), 7.31-7.33 (m, 2H), 7.55 (dd, J=2.2 Hz, 6.6 Hz, 2H). $^{13}$C NMR (75 MHz, CDCl$_3$) δ=55.9, 65.2, 87.0, 89.7, 114.6, 123.1, 128.8, 128.9, 129.1, 132.3, 133.6, 160.2.

4,4-Dimethyl-1-phenyl-pent-1-yn-3-ol (Emmerson, D. P. G.; Hems, P. W.; Davis, B. G. *Org. Lett.* 2006, 8, 207-210). $^1$H NMR (300 MHz, CDCl$_3$) δ=1.06 (s, 9H), 2.25 (d, J=5.4 Hz, 1H), 4.23 (d, J=5.4 Hz, 1H), 7.26-7.29 (m, 3H), 7.41-7.44 (m, 2H). $^{13}$C NMR (75 MHz, CDCl$_3$) δ=26.0, 36.7, 72.4, 86.3, 89.7, 123.4, 128.8, 128.9, 132.3.

1-Cyclohexyl-3-phenyl-prop-2-yn-1-ol (Takita, R.; Yakura, K.; Ohshima, T.; Shibasaki, M. *J. Am. Chem. Soc.* 2005, 127, 13760-13761). $^1$H NMR (300 MHz, CDCl$_3$) δ=1.08-1.38 (m, 5H), 1.58-1.74 (m, 2H), 1.75-1.76 (m, 2H), 1.78-1.93 (m, 2H), 2.58 (bs, 1H), 4.39 (d, J=4.9 Hz, 1H), 7.27-7.29 (m, 3H), 7.41-7.44 (m, 2H). $^{13}$C NMR (75 MHz, CDCl$_3$) δ=26.4, 26.5, 27.0, 28.8, 29.3, 44.9, 68.2, 86.2, 90.0, 123.4, 128.8, 128.9, 132.3.

1-(4-Fluorophenyl)-3-trimethylsilyl-prop-2-yn-1-ol (Yamabe, H.; Mizuno, A.; Kusama, H.; Iwasawa, N. *J. Am. Chem. Soc.* 2005, 127, 3248-3249). $^1$H NMR (300 MHz, CDCl$_3$) δ=0.23 (s, 9H), 2.41 (d, J=5.9 Hz, 1H), 5.45 (d, J=5.9 Hz, 1H), 7.06-7.12 (m, 2H), 7.52-7.57 (m, 2H). $^{13}$C NMR (75 MHz, CDCl$_3$) δ=0.5, 64.9, 92.6, 105.4, 116.1 (d, $J_{C,F}$=21.3 Hz), 129.3 (d, $J_{C,F}$=8.6 Hz), 136.8 (d, $J_{C,F}$=3.0 Hz), 163.4 (d, $J_{C,F}$=246.8 Hz).

1-(3-Methoxyphenyl)-3-trimethylsilyl-prop-2-yn-1-ol (Shi Shun, A. L. K.; Chemick, E. T.; Eisler, S.; Tykwinski, R. R. *J. Org. Chem.* 2003, 68, 1339-1347). $^1$H NMR (300 MHz, CDCl$_3$) δ=0.20 (s, 9H), 2.44 (d, J=5.9 Hz, 1H), 3.81 (s, 3H), 5.41 (d, J=5.9 Hz, 1H), 6.87 (m, 1H), 7.10-7.13 (m, 2H), 7.28 (m, 1H). $^{13}$C NMR (75 MHz, CDCl$_3$) δ=0.4, 55.9, 65.5, 92.2, 105.6, 112.7, 114.8, 119.7, 130.3, 142.5, 160.4.

1-(3-Fluorophenyl)-3-trimethylsilyl-prop-2-yn-1-ol. $^1$H NMR (300 MHz, CDCl$_3$) δ=0.21 (s, 9H), 2.52 (d, J=5.9 Hz, 1H), 5.43 (d, J=5.9 Hz, 1H), 7.01 (m, 1H), 7.24-7.34 (m, 3H). $^{13}$C NMR (75 MHz, CDCl$_3$) δ=0.4, 64.9, 92.7, 105.0, 114.4 (d, $J_{C,F}$=22.3 Hz), 115.9 (d, $J_{C,F}$=21.2 Hz), 112.9 (d, $J_{C,F}$=2.5

Hz), 130.7 (d, $J_{C,F}$=8.1 Hz), 143.4 (d, $J_{C,F}$=7.1 Hz), 163.5 (d, $J_{C,F}$=246.3 Hz). Anal. Calcd. $C_{12}H_{15}FOSi$: C, 64.83; H, 6.80. Found: C, 64.73; H, 6.92.

1-Phenyl-3-trimethylsilyl-prop-2-yn-1-ol (Nakamura, S.; Kusuda, S.; Kawamura, K.; Toru, T. J. Org. Chem. 2002, 67, 640-647). $^1$H NMR (300 MHz, CDCl$_3$) δ=0.22 (s, 9H), 2.65 (d, J=6.4 Hz, 1H), 5.43 (d, J=6.4 Hz, 1H), 7.31-7.40 (m, 3H), 7.51-7.55 (m, 2H). $_{13}$C NMR (75 MHz, CDCl$_3$) δ=0.5, 65.5, 92.1, 105.7, 127.4, 128.9, 129.2, 140.9.

3-(Dimethylphenylsilyl)-1-(4-fluorophenyl)-prop-2-yn-1-ol. $^1$H NMR (300 MHz, CDCl$_3$) δ=0.48 (s, 6H), 2.67 (bs, 1H), 5.47 (s, 1H), 7.04 (dd, J=8.8 Hz, 8.8 Hz, 2H), 7.38-7.41 (m, 3H), 7.50-7.55 (m, 2H), 7.64-7.67 (m, 2H). $^{13}$C NMR (75 MHz, CDCl$_3$) δ=−0.4, 64.9, 90.5, 107.2, 116.1 (d, $J_{C,F}$=21.7 Hz), 128.6, 129.2 (d, $J_{C,F}$=8.1 Hz), 130.3, 134.3, 136.6 (d, $J_{C,F}$=3.0 Hz), 137.0, 163.3 (d, $J_{C,F}$=247.3 Hz). Anal. Calcd. $C_{17}H_{17}FOSi$: C, 71.79; H, 6.02. Found: C, 71.40; H, 5.56.

1-(4-Fluorophenyl)-3-triphenylsilyl-prop-2-yn-1-ol. $^1$H NMR (300 MHz, CDCl$_3$) δ=2.41 (bs, 1H), 5.55 (s, 1H), 7.03 (dd, J=8.8 Hz, 8.8 Hz, 2H), 7.03-7.42 (m, 9H), 7.52-7.57 (m, 2H), 7.61-7.65 (m, 6H). $^{13}$C NMR (75 MHz, CDCl$_3$) δ=65.2, 87.9, 110.0, 116.2 (d, $J_{C,F}$=21.7 Hz), 128.7, 129.3 (d, $J_{C,F}$=8.1 Hz), 130.8, 133.6, 136.2, 136.5 (d, $J_{C,F}$=3.0 Hz), 163.0 (d, $J_{C,F}$=247.3 Hz). Anal. Calcd. $C_{27}H_{21}FOSi$: C, 79.38; H, 5.18. Found: C, 79.01; H, 4.98.

INCORPORATION BY REFERENCE

All of the other U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A $C_2$-symmetric chiral bisoxazolidine represented by formula III,:

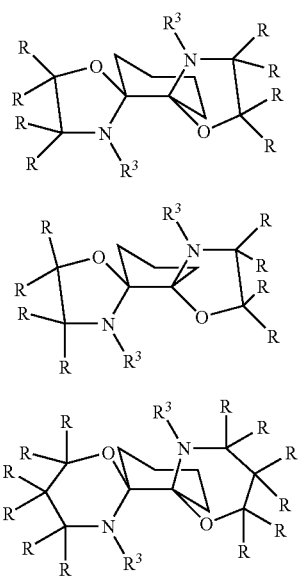

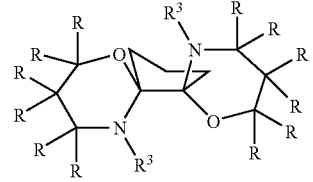

wherein,
R is, independently for each occurrence, hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, or ester; or any two adjacent R, taken together with the —C—C— fragment to which they are bound, is a carbocyclic moiety, a heterocyclic moiety, an aromatic moiety, or a heteroaromatic moiety; and
$R^3$ is hydrogen, alkyl, alkenyl, alkynyl, aryl, aralkyl, heteroaryl, heteroaralkyl, heterocyclic, or heterocycloalkyl.

2. A $C_2$-symmetric chiral bisoxazolidine represented by formula VII:

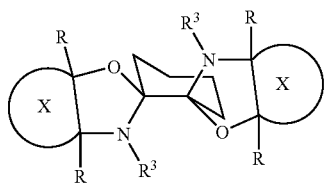

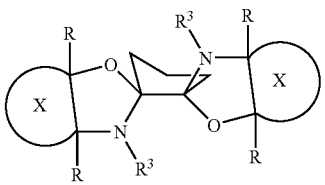

wherein,
R is hydrogen, alkyl, alkenyl, aryl, cycloalkyl, aralkyl, heteroalkyl, halogen, hydroxy, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, or ester;
$R^3$ is hydrogen, alkyl, alkenyl, alkynyl, aryl, aralkyl, heteroaryl, heteroaralkyl, heterocyclic, or heterocycloalkyl; and

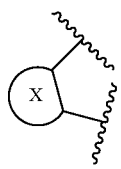

a carbocyclic moiety, a heterocyclic moiety, an aromatic moiety, or a heteroaromatic moiety.

3. The bisoxazolidine of claim 2, wherein $R^3$ is hydrogen.
4. The bisoxazolidine of claim 2, wherein R is hydrogen.

5. The bisoxazolidine of claim 2, wherein $R^3$ is hydrogen; and
R is hydrogen.
6. A $C_2$-symmetric chiral
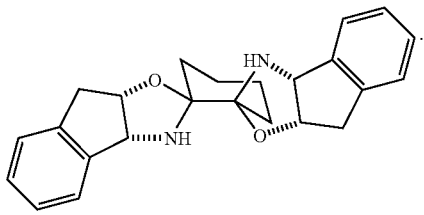
bisoxazolidine represented by.
7. The bisoxazolidine of claim 1, wherein $R^3$ is hydrogen.
8. The bisoxazolidine of claim 2, wherein
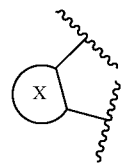
carbocyclic moiety.
9. The bisoxazolidine of claim 2, wherein
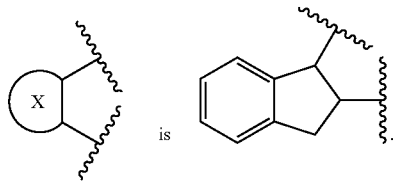 is
10. The bisoxazolidine of claim 2, wherein $R^3$ is hydrogen; and
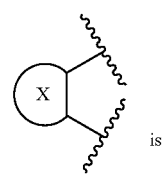 is
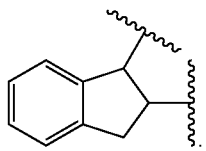
* * * * *

UNITED STATES PATENT AND TRADEMARK OFFICE
CERTIFICATE OF CORRECTION

PATENT NO. : 7,763,734 B2
APPLICATION NO. : 11/737371
DATED : July 27, 2010
INVENTOR(S) : Christian Wolf et al.

It is certified that error appears in the above-identified patent and that said Letters Patent is hereby corrected as shown below:

In Claim 1, column 33, line 52 – column 34, line 10, omit

IV

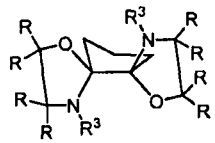

V

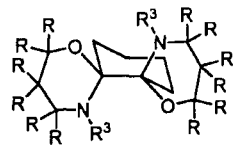

VII

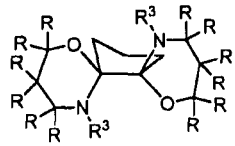

" ".

In Claim 2, lines 36-44, omit

VIII

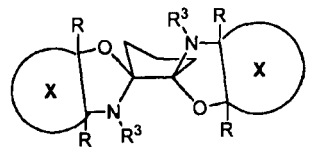

" ".

Signed and Sealed this

Fourteenth Day of September, 2010

David J. Kappos
*Director of the United States Patent and Trademark Office*

CERTIFICATE OF CORRECTION (continued)
U.S. Pat. No. 7,763,734 B2

In Claim 6, line 6, insert --bisoxazolidine represented by-- after the term "chiral".

In Claim 6, line 19, omit "bisoxazolidine represented by".

UNITED STATES PATENT AND TRADEMARK OFFICE
CERTIFICATE OF CORRECTION

PATENT NO. : 7,763,734 B2  Page 1 of 2
APPLICATION NO. : 11/737371
DATED : July 27, 2010
INVENTOR(S) : Christian Wolf et al.

It is certified that error appears in the above-identified patent and that said Letters Patent is hereby corrected as shown below:

In Claim 1, column 33, line 52 – column 34, line 10, omit

IV

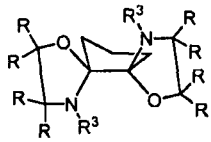

V

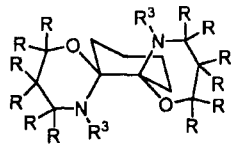

VII

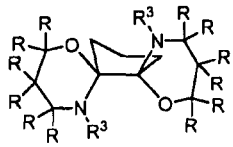

" ".

In Claim 2, column 34, lines 36-44, omit

VIII

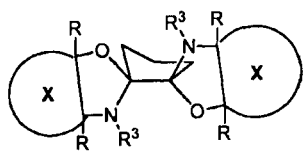

" ".

This certificate supersedes the Certificate of Correction issued September 14, 2010.

Signed and Sealed this

Second Day of November, 2010

David J. Kappos
*Director of the United States Patent and Trademark Office*

In Claim 6, column 35, line 6, insert --bisoxazolidine represented by-- after the term "chiral".

In Claim 6, column 35, line 19, omit "bisoxazolidine represented by".